United States Patent
Geiger et al.

(10) Patent No.: US 12,007,301 B2
(45) Date of Patent: Jun. 11, 2024

(54) VARIABLE COMPOSITION GAS MIXTURE SENSOR

(71) Applicant: ClearSign Technologies Corporation, Seattle, WA (US)

(72) Inventors: Robert Geiger, Seattle, WA (US); Jackson Matthew Pleis, Carnation, WA (US); Donald Kendrick, Bellevue, WA (US); Christopher A. Wiklof, Everett, WA (US)

(73) Assignee: ClearSign Technologies Corporation, Tulsa, OK (US)

( * ) Notice: Subject to any disclaimer, the term of this patent is extended or adjusted under 35 U.S.C. 154(b) by 243 days.

(21) Appl. No.: 17/135,517

(22) Filed: Dec. 28, 2020

(65) Prior Publication Data
US 2021/0255063 A1 Aug. 19, 2021

Related U.S. Application Data

(63) Continuation of application No. PCT/US2019/039467, filed on Jun. 27, 2019.
(Continued)

(51) Int. Cl.
*G01M 15/14* (2006.01)
*F23D 11/40* (2006.01)
(Continued)

(52) U.S. Cl.
CPC ........... *G01M 15/14* (2013.01); *F23D 11/406* (2013.01); *F23D 14/145* (2013.01); *F23N 1/022* (2013.01);
(Continued)

(58) Field of Classification Search
CPC ........... G01N 33/0027; G01N 33/0062; G01N 33/0073
See application file for complete search history.

(56) References Cited

U.S. PATENT DOCUMENTS

| 5,439,374 | A | 8/1995 | Jamieson |
| 7,559,234 | B1 * | 7/2009 | Chorpening ........ G01M 15/102 700/274 |

(Continued)

FOREIGN PATENT DOCUMENTS

| EP | 2591289 B1 | 7/2011 |
| WO | 2015123683 A1 | 8/2015 |

(Continued)

OTHER PUBLICATIONS

PCT International Search Report and Written Opinion for International Application No. PCT/US2019/039467 dated Oct. 21, 2019, 16 pgs.

(Continued)

*Primary Examiner* — John Kwon
(74) *Attorney, Agent, or Firm* — Launchpad IP, Inc.; Christopher A. Wiklof; James C. Larsen

(57) ABSTRACT

A system for measuring a fuel-oxidant equivalence ratio includes at least one wall defining a gas volume including fuel and air. A gas ionization source is configured to cause a formation of ions in the gas. A power supply is configured to output a time-varying voltage. A first electrode is disposed in the gas volume, operatively coupled to the power supply, and configured to carry the time-varying voltage. A second electrode is arranged to operatively couple to a signal output by the first electrode after the signal passes through the gas volume. Characteristics of the received signal indicate the fuel-oxidant equivalence ratio.

40 Claims, 11 Drawing Sheets

Related U.S. Application Data

(60) Provisional application No. 62/821,543, filed on Mar. 21, 2019, provisional application No. 62/756,468, filed on Nov. 6, 2018, provisional application No. 62/702,475, filed on Jul. 24, 2018, provisional application No. 62/694,890, filed on Jul. 6, 2018, provisional application No. 62/691,469, filed on Jun. 28, 2018.

(51) Int. Cl.
*F23D 14/14* (2006.01)
*F23N 1/02* (2006.01)
*F23N 5/02* (2006.01)
*F23N 5/12* (2006.01)
*F23N 5/18* (2006.01)
*G01N 33/00* (2006.01)

(52) U.S. Cl.
CPC ............ *F23N 5/022* (2013.01); *F23N 5/123* (2013.01); *F23N 5/184* (2013.01); *G01N 33/0027* (2013.01); *G01N 33/0062* (2013.01); *G01N 33/0073* (2013.01); *F23D 2208/10* (2013.01); *F23D 2212/103* (2013.01); *F23N 2237/26* (2020.01)

(56) References Cited

U.S. PATENT DOCUMENTS

| | | |
|---|---|---|
| 2005/0250061 A1 | 11/2005 | Lochschmied |
| 2013/0139578 A1 | 6/2013 | Hoehne et al. |
| 2014/0045128 A1 | 2/2014 | Lee et al. |
| 2015/0141240 A1* | 5/2015 | Roller .................. B05C 19/00 118/47 |
| 2015/0204239 A1* | 7/2015 | Minto .................. F02C 7/228 60/741 |
| 2015/0226133 A1* | 8/2015 | Minto .................. F02C 9/48 60/39.27 |
| 2016/0298836 A1 | 10/2016 | Colannino et al. |
| 2018/0003083 A1* | 1/2018 | Huntington ............ F02C 6/18 |
| 2018/0003378 A1 | 1/2018 | Karkow et al. |

FOREIGN PATENT DOCUMENTS

| | | |
|---|---|---|
| WO | 2015123701 A1 | 8/2015 |
| WO | 2016140681 A1 | 9/2016 |

OTHER PUBLICATIONS

PCT International Preliminary Report on Patentability for International Application No. PCT/US2019/039467 dated Dec. 29, 2020, 11 pgs.

* cited by examiner

VARIABLE COMPOSITION GAS MIXTURE SENSOR

CROSS REFERENCE TO RELATED APPLICATIONS

The present application is a Continuation that claims priority benefit from co-pending PCT Application No. PCT/US2019/039467 entitled "VARIABLE COMPOSITION GAS MIXTURE SENSOR", filed Jun. 27, 2019. PCT Application No. PCT/US2019/039467 claims priority benefit from U.S. Provisional Patent Application No. 62/702,475, entitled "VARIABLE COMPOSITION GAS MIXTURE SENSOR," filed Jul. 24, 2018; from U.S. Provisional Patent Application No. 62/756,468, entitled "PILOT BURNER WITH A FLAME SENSOR," filed Nov. 6, 2018; from U.S. Provisional Patent Application No. 62/821,543, entitled "COMBUSTION SYSTEM INCLUDING A COMBUSTION SENSOR AND A PLASMA GENERATOR," filed Mar. 21, 2019; from U.S. Provisional Patent Application No. 62/694,890, entitled "INDUSTRIAL BURNER INCLUDING A LOW TEMPERATURE PLASMA STABILIZED FLAME HOLDER," filed Jul. 6, 2018; and from U.S. Provisional Patent Application No. 62/691,469, entitled "BURNER SYSTEM INCLUDING A PERFORATED FLAME HOLDER AND ELECTRO-CAPACITIVE SENSING," filed Jun. 28, 2018. Each of the foregoing applications, to the extent not inconsistent with the disclosure herein, is incorporated by reference in its entirety.

The present application is related to U.S. patent application Ser. No. 17/135,517, entitled, "BURNER INCLUDING AN ELECTRICAL PERMITTIVITY OR ELECTRICAL CAPCITANCE FLAME SENSOR,", filed contemporaneousy herewith.

SUMMARY

An equivalence ratio, referred to by the variable phi (ct:>), is a dimensionless number that expresses a ratio of fuel-to-oxidant present in a gas relative to a stoichiometric ratio of fuel-to-oxidant in a combustion reaction.

For example, a completed combustion reaction of methane and oxygen may be expressed as:

$$CH_4 + 2O_2 \rightarrow CO_2 + 2H_2O$$

In this complete combustion reaction, the stoichiometric ratio of fuel-to-oxygen is 0.5. That is, the combustion reaction requires two oxygen molecules for every methane molecule.

Phi may be expressed as:

$$ct :> = \frac{\text{Molar Fuel Concentration/Molar Oxidant Concentration}}{\text{Fuel/Oxidant Stoichiometric Ration}}$$

For example, if there are 3 moles of oxygen for each mole of methane in a gas, phi may be solved as:

$$CD_{example} = \frac{1/3}{.5} = \frac{.33}{.50} = 0.667$$

Equivalence ratio is important because it is predictive of flammability—a fuel is flammable only between a lower and an upper limit of phi, limits which may be referred to respectively as lower and upper flammability limits. For safety purposes, it may be desirable to maintain phi in a tank or in a headspace in industrial equipment either below the lower flammability limit or above the upper flammability limit, such mixtures not being prone to detonation or conflagration.

Equivalence ratio is also important because it is predictive of industrial burner performance.

According to an embodiment, a system for measuring a fuel-oxidant equivalence ratio includes at least one wall defining a gas volume including fuel and air. A gas ionization source is configured to cause a formation of ions in the gas. A power supply is configured to output a time-varying voltage. A first electrode is disposed in the gas volume, operatively coupled to the power supply, and configured to carry the time-varying voltage. A second electrode is arranged to receive a signal from the first electrode through at least a portion of the gas volume. A receiver circuit is operatively coupled to the second electrode and configured to receive the signal having a characteristic corresponding to the fuel-oxidant equivalence ratio within the gas volume. A control circuit is operatively coupled to the receiver circuit and configured to determine a value corresponding to the fuel-oxidant equivalence ratio. In embodiments, the system includes a temperature and/or pressure sensor operatively coupled to the control circuit. In embodiments, the gas ionization source includes a flame source, such as an industrial burner, or an electrode (e.g., dielectric barrier layer or corona) ion source. In one embodiment, the control circuit includes a transducer circuit. According to an embodiment, a method for measuring a fuel-oxidant equivalence ratio includes causing ion formation in a gas including fuel and oxidant, applying a periodic voltage signal to a first electrode adjacent to the gas, and receiving a periodic response signal through the gas with a second electrode. The periodic response signal may be produced according to a response of the ions and electrons to the periodic voltage signal. The method includes converting the periodic response signal to a corresponding DC signal that is converted to a digital signal, receiving a sensor signal corresponding to an parameter of the gas, applying the digital signal and the sensor signal as arguments for a function, and determining a value of the function corresponding to the fuel-oxidant equivalence ratio.

DETAILED DESCRIPTION

Figure 1A:
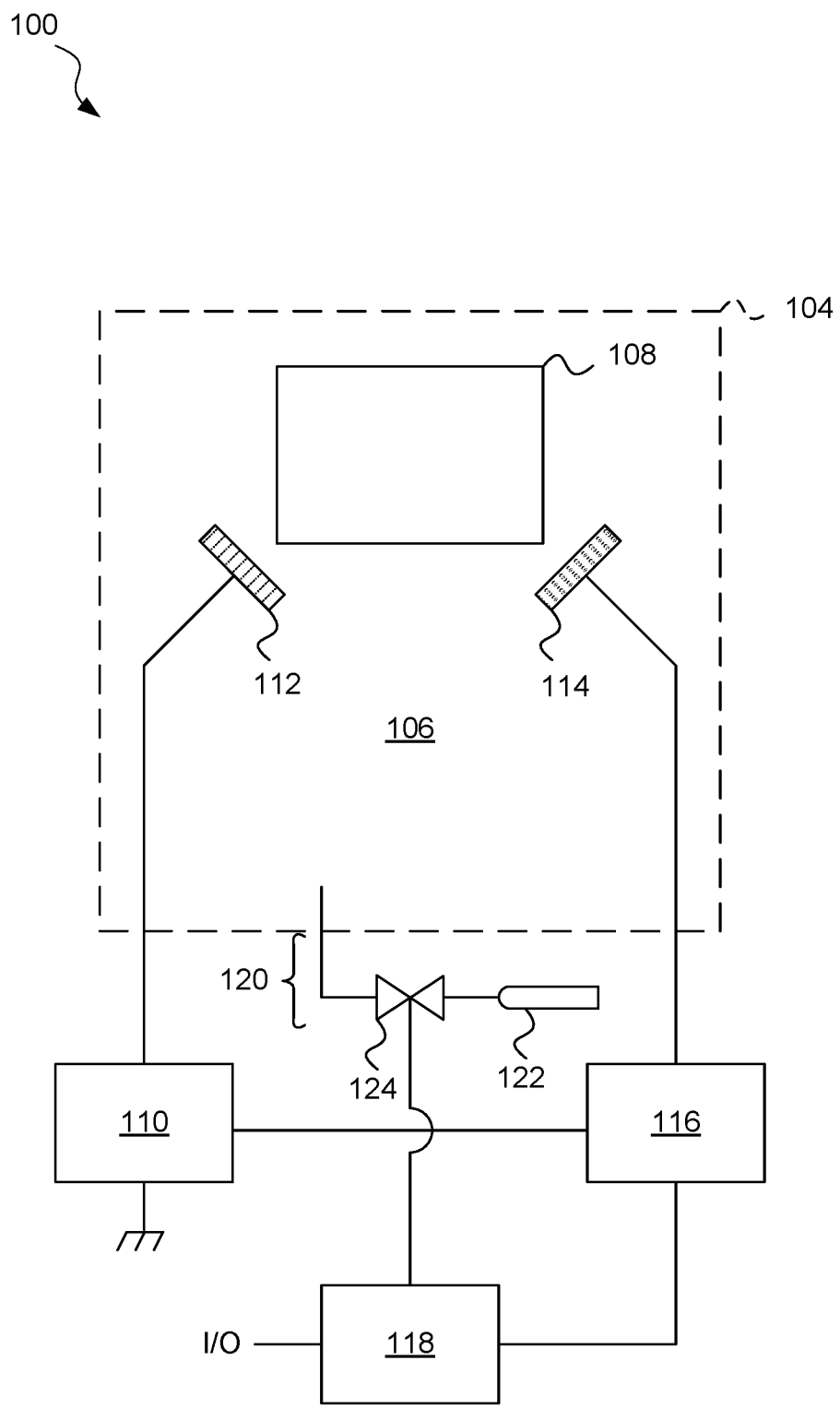
FIG. 1A is a diagram of a system for measuring a fuel-oxidant equivalence ratio, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1A is a diagram of a system 100 for measuring a fuel-oxidant equivalence ratio, according to an embodiment. The system 100 may include at least one wall 104 defining a gas volume 106. The system 100 includes a gas ionization source 108 configured to cause a formation of ions in a gas. A power supply 110 is configured to output a time-varying voltage, according to an embodiment. The system 100 may include a first electrode 112 disposed in the gas volume 106, operatively coupled to the power supply 110, and configured to carry the time-varying voltage. The system 100 may include a second electrode 114, arranged to operatively couple to a signal from the first electrode 112 through at least a portion of the gas volume 106, according to an embodiment. The system 100 may include a receiver circuit 116 operatively coupled to the second electrode 114 and configured to receive the signal. The signal may have a characteristic corresponding to a fuel-oxidant equivalence ratio within the gas volume 106, according to an embodiment. The system 100 may include a control circuit 118 operatively coupled to the receiver circuit 116 and configured to determine a value corresponding to the fuel-oxidant equivalence ratio.

According to an embodiment, the gas ionization source 108 may occupy a physical volume within the gas volume 106. The first and the second electrodes 112, 114 may be aligned such that the received signal has a characteristic corresponding to the fuel-oxidant equivalence ratio within the gas volume 106.

According to an embodiment, the gas ionization source 108 may include at least one ionization electrode configured to ionize the gas in the gas volume 106 to form ions. Ionizing the gas may also include introducing free electrons.

Various electrode configurations and types are contemplated. According to an embodiment, the at least one ionization electrode may include a corona electrode and/or a dielectric barrier electrode.

According to an embodiment, the gas volume 106 may include a fuel tank headspace.

In some applications, the gas volume 106 may be vented to the atmosphere. In other applications, a refinery or a chemical plant may be susceptible to an accumulation of air or other oxidant in gas volume spaces 106 otherwise occupied by a fuel or a fuel vapor. If the oxidant (e.g., atmospheric oxygen) is present in a proportion (aka equivalence ratio) that falls within flammability limits of the fuel, a hazardous condition may be inferred to exist. Corrective action may be taken to reduce the hazard.

Referring to FIG. 1A, the control circuit 118 may be further configured to automatically take corrective action when the fuel-oxidant equivalence ratio is determined to be within the flammability limits, according to an embodiment.

According to an embodiment, the system 100 further may include a purging system 120. The control circuit 118 may be configured to actuate the purging system 120 to purge fuel vapor and/or oxidant from the gas volume 106 when the fuel-oxidant equivalence ratio is determined to be within the flammability limits, according to an embodiment.

According to an embodiment, the purging system 120 may include an inert gas source 122 and a purge control valve 124. The control circuit 118 may be configured to actuate the purge control valve 124 when the fuel-oxidant equivalence ratio is determined to be within the flammability limits, according to an embodiment. For example, the inert gas source 122 may include a pressure tank holding an inert (i.e., non-oxidant) gas such as nitrogen, helium, or carbon dioxide.

Referring to FIG. 1A, the wall 104 may include a fuel tank. Additionally or alternatively, the wall 104 may include a flame arrestor, according to an embodiment.

According to an embodiment, the fuel-oxidant equivalence ratio is a fuel-air equivalence ratio.

Figure 1B:
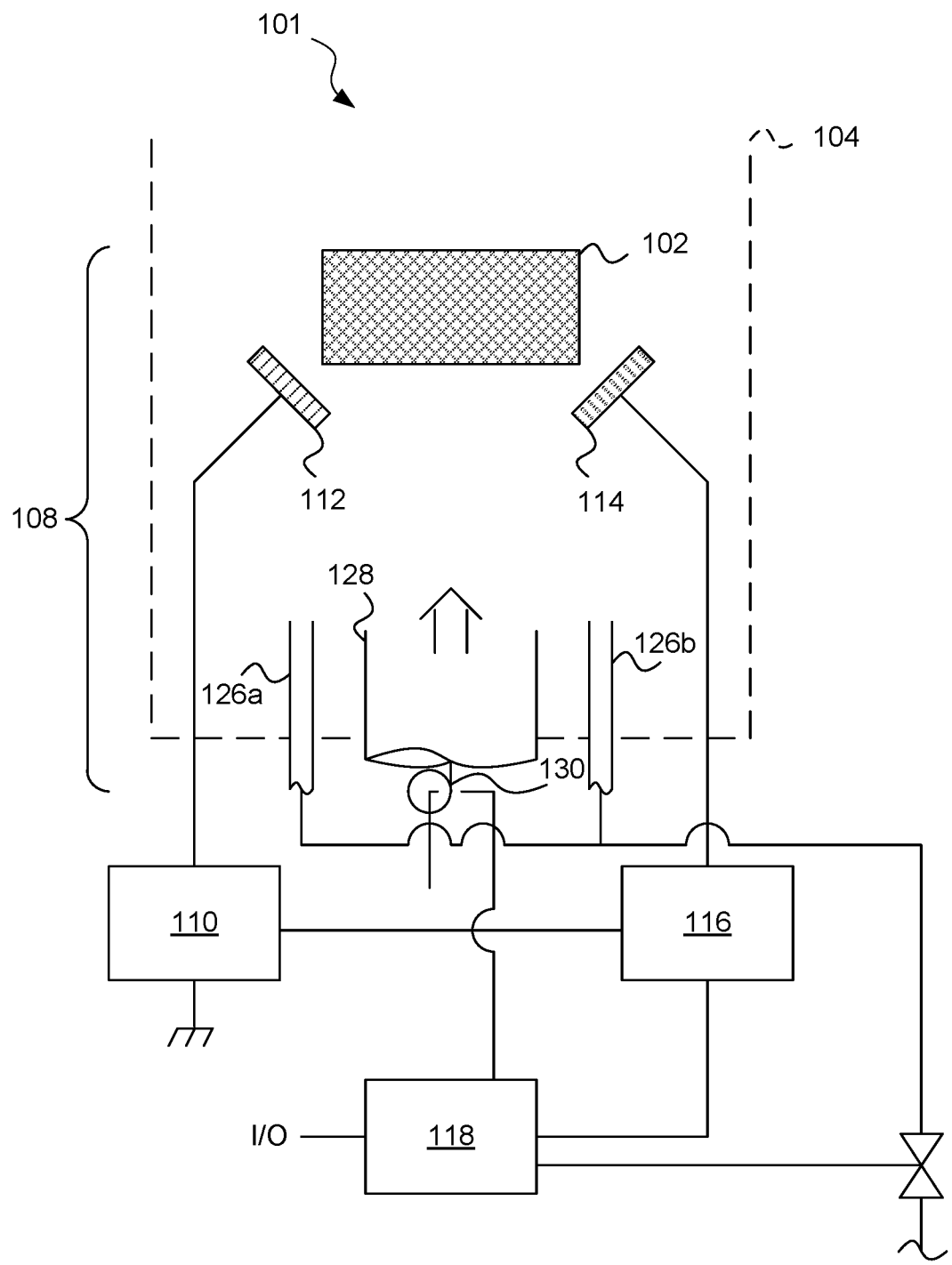
FIG. 1B is a block diagram of a system for measuring a fuel-oxidant equivalence ratio wherein a gas ionization source includes a burner, according to an embodiment.

FIG. 1B is a block diagram of a system 101 for measuring the fuel-air equivalence ratio wherein the gas ionization source 108 includes a burner, according to an embodiment.

According to an embodiment, the gas ionization source 108 may include an industrial burner.

According to an embodiment, the burner 108 may include a flame holder 102 aligned to receive a mixture of fuel from a fuel source 126a, 126b and combustion air from a combustion air source 128, and to hold a combustion reaction supported by the fuel and the combustion air.

According to an embodiment, the burner 108 further may include a blower 130. The control circuit 118 may be configured to control the blower 130 output responsive to detecting the fuel-oxidant equivalence ratio, according to an embodiment. According to embodiments, the control circuit 118 includes a program carried by a non-transitory computer memory medium configured to cause the control circuit 118 to keep the fuel-oxidant equivalence ratio within the flammability limits of the fuel. Accordingly, the system 101 may be configured to maintain more stable combustion compared to a burner system that does not include an equivalence ratio sensor.

According to an embodiment, the burner 108 may further include an air register. The control circuit 118 may be configured to control the air register, according to an embodiment.

According to an embodiment, the flame holder 102 comprises a perforated flame holder 102.

Figure 2:
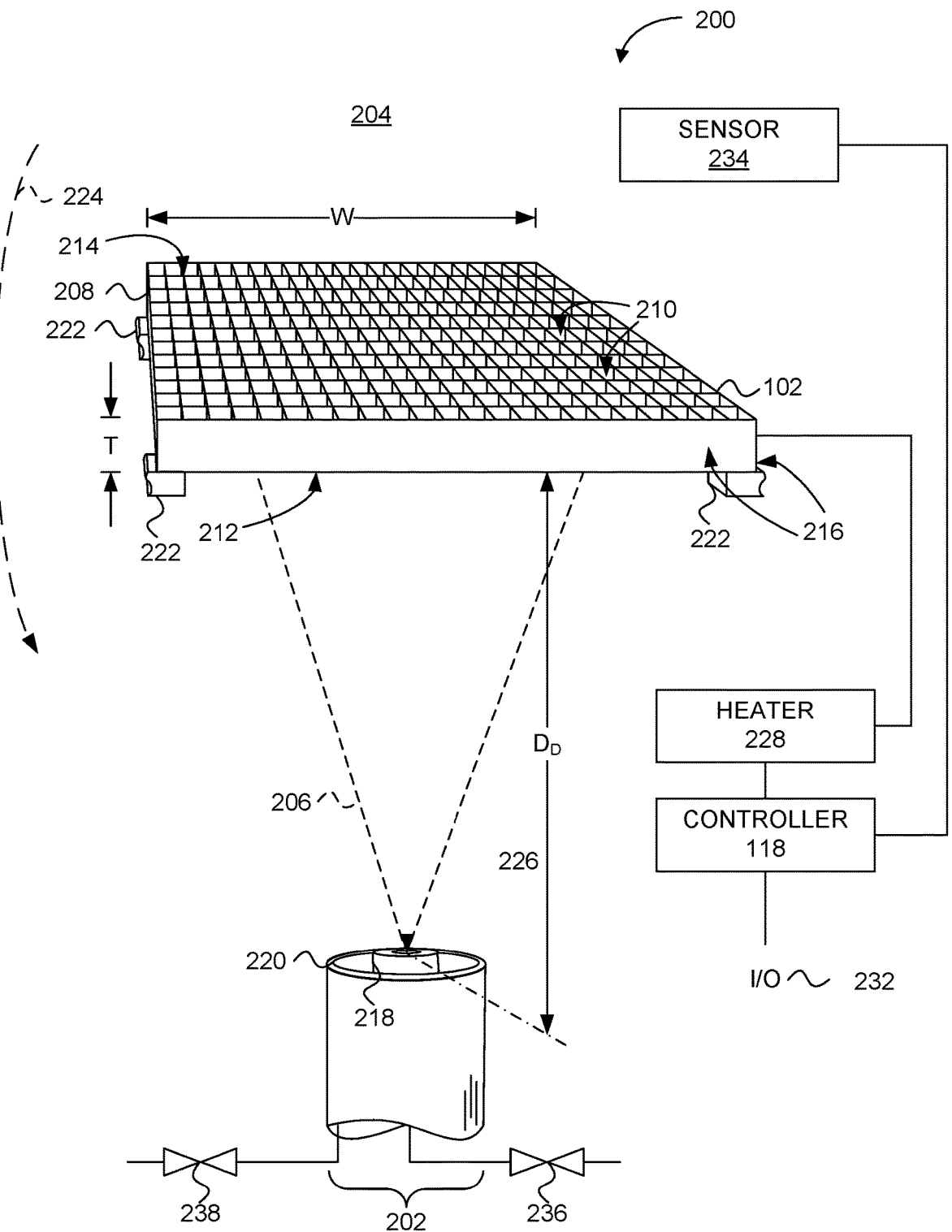
FIG. 2 is a simplified diagram of a burner system including a perforated flame holder configured to hold a combustion reaction, according to an embodiment.

FIG. 2 is a simplified diagram of a burner system 200 including a perforated flame holder 102 configured to hold a combustion reaction, according to an embodiment. As used herein, the terms perforated flame holder, perforated reaction holder, porous flame holder, porous reaction holder, duplex, and duplex tile shall be considered synonymous unless further definition is provided.

Experiments performed by the inventors have shown that perforated flame holders 102 described herein can support very clean combustion. Specifically, in experimental use of burner systems 200 ranging from pilot scale to full scale, output of oxides of nitrogen (NOx) was measured to range from low single digit parts per million (ppm) down to undetectable (less than 1 ppm) concentration of NOx at the stack. These remarkable results were measured at 3% (dry) oxygen ($O_2$) concentration with undetectable carbon monoxide (CO) at stack temperatures typical of industrial furnace applications (1400-1600° F.). Moreover, these results did not require any extraordinary measures such as selective catalytic reduction (SCR), selective non-catalytic reduction (SNCR), water/steam injection, external flue gas recirculation (FGR), or other heroic extremes that may be required for conventional burners to even approach such clean combustion.

According to embodiments, the burner system 200 includes a fuel and oxidant source 202 disposed to output fuel and oxidant into a combustion volume 204 to form a fuel and oxidant mixture 206. As used herein, the terms fuel and oxidant mixture and fuel stream may be used interchangeably and considered synonymous depending on the context, unless further definition is provided. As used herein, the terms combustion volume, combustion chamber, furnace volume, and the like shall be considered synonymous unless further definition is provided. The perforated flame holder 102 is disposed in the combustion volume 204 and positioned to receive the fuel and oxidant mixture 206.

Figure 3:
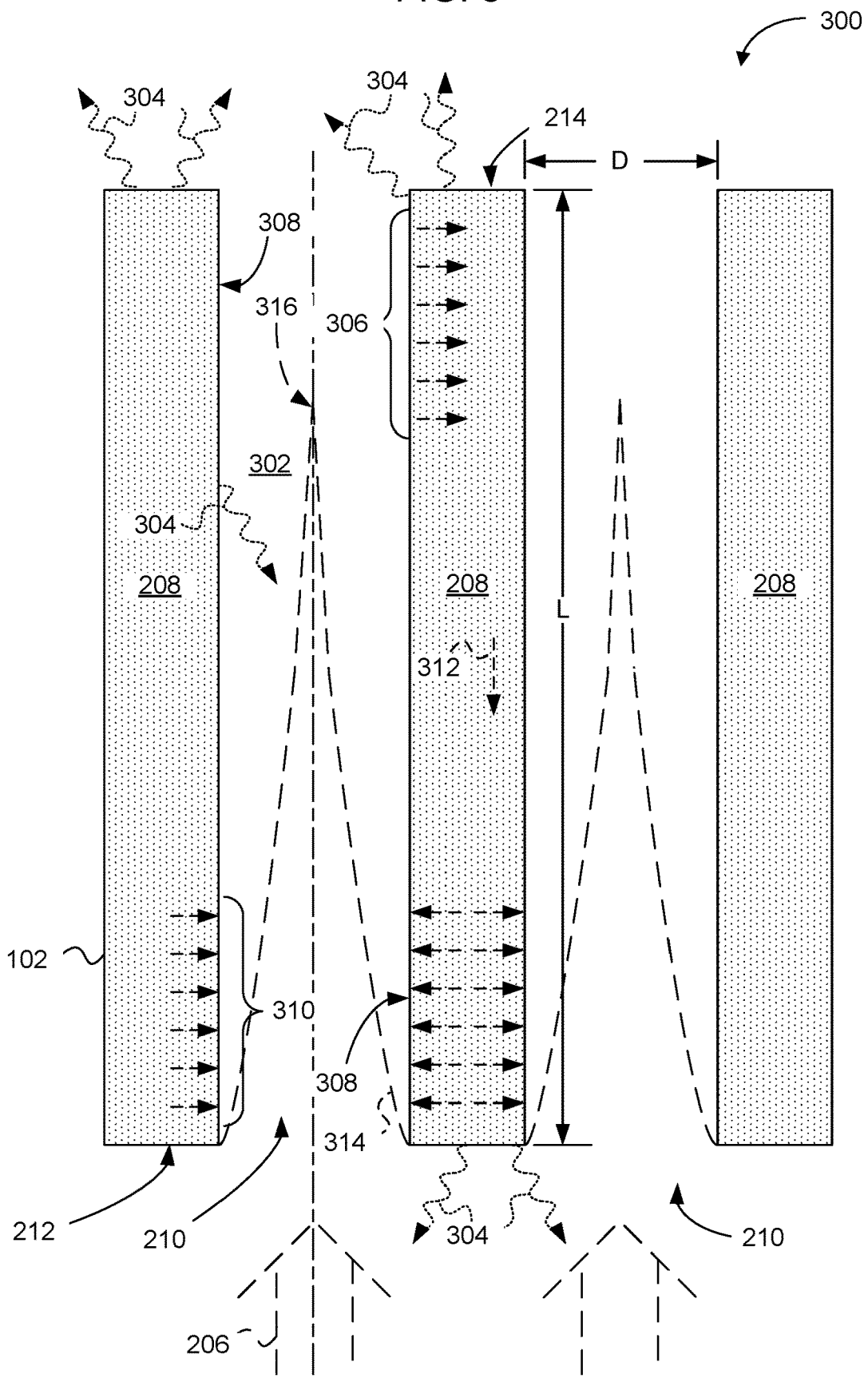
FIG. 3 is a side sectional diagram of a portion of the perforated flame holder of FIGS. 1A-B and 2, according to an embodiment.

FIG. 3 is a side sectional diagram 300 of a portion of the perforated flame holder 102 of FIGS. 1A, 1B and 2, according to an embodiment. Referring to FIGS. 2 and 3, the perforated flame holder 102 includes a perforated flame holder body 208 defining a plurality of perforations 210 aligned to receive the fuel and oxidant mixture 206 from the fuel and oxidant source 202. As used herein, the terms perforation, pore, aperture, elongated aperture, and the like, in the context of the perforated flame holder 102, shall be considered synonymous unless further definition is provided. The perforations 210 are configured to collectively hold a combustion reaction 302 supported by the fuel and oxidant mixture 206.

The fuel can include hydrogen, a hydrocarbon gas, a vaporized hydrocarbon liquid, an atomized hydrocarbon liquid, or a powdered or pulverized solid. The fuel can be a single species or can include a mixture of gas(es), vapor(s), atomized liquid(s), and/or pulverized solid(s). For example, in a process heater application the fuel can include fuel gas or byproducts from the process that include carbon monoxide (CO), hydrogen (H2), and methane (CH4). In another application the fuel can include natural gas (mostly CH4) or propane (C3H8). In another application, the fuel can include #2 fuel oil or #6 fuel oil. Dual fuel applications and flexible fuel applications are similarly contemplated by the inventors. The oxidant can include oxygen carried by air, flue gas, and/or can include another oxidant, either pure or carried by a carrier gas. The terms oxidant and oxidizer shall be considered synonymous herein.

According to an embodiment, the perforated flame holder body 208 can be bounded by an input face 212 disposed to receive the fuel and oxidant mixture 206, an output face 214 facing away from the fuel and oxidant source 202, and a peripheral surface 216 defining a lateral extent of the perforated flame holder 102. The plurality of perforations 210 which are defined by the perforated flame holder body 208 extend from the input face 212 to the output face 214. The plurality of perforations 210 can receive the fuel and oxidant mixture 206 at the input face 212. The fuel and oxidant mixture 206 can then combust in or near the plurality of perforations 210 and combustion products can exit the plurality of perforations 210 at or near the output face 214.

According to an embodiment, the perforated flame holder 102 is configured to hold a majority of the combustion reaction 302 within the perforations 210. For example, on a steady-state basis, more than half the molecules of fuel output into the combustion volume 204 by the fuel and oxidant source 202 may be converted to combustion products between the input face 212 and the output face 214 of the perforated flame holder 102. According to an alternative interpretation, more than half of the heat or thermal energy output by the combustion reaction 302 may be output between the input face 212 and the output face 214 of the perforated flame holder 102. As used herein, the terms heat, heat energy, and thermal energy shall be considered synonymous unless further definition is provided. As used above, heat energy and thermal energy refer generally to the released chemical energy initially held by reactants during the combustion reaction 302. As used elsewhere herein, heat, heat energy and thermal energy correspond to a detectable temperature rise undergone by real bodies characterized by heat capacities. Under nominal operating conditions, the perforations 210 can be configured to collectively hold at least 80% of the combustion reaction 302 between the input face 212 and the output face 214 of the perforated flame holder 102. In some experiments, the inventors produced a combustion reaction 302 that was apparently wholly contained in the perforations 210 between the input face 212 and the output face 214 of the perforated flame holder 102. According to an alternative interpretation, the perforated flame holder 102 can support combustion between the input face 212 and output face 214 when combustion is "time-averaged." For example, during transients, such as before the perforated flame holder 102 is fully heated, or if too high a (cooling) load is placed on the system, the combustion may travel somewhat downstream from the output face 214 of the perforated flame holder 102. Alternatively, if the cooling load is relatively low and/or the furnace temperature reaches a high level, the combustion may travel somewhat upstream of the input face 212 of the perforated flame holder 102.

While a "flame" is described in a manner intended for ease of description, it should be understood that in some instances, no visible flame is present. Combustion occurs primarily within the perforations 210, but the "glow" of combustion heat is dominated by a visible glow of the perforated flame holder 102 itself. In other instances, the inventors have noted transient "huffing" or "flashback" wherein a visible flame momentarily ignites in a region lying between the input face 212 of the perforated flame holder 102 and the fuel nozzle 218, within the dilution region $D_O$. Such transient huffing or flashback is generally short in duration such that, on a time-averaged basis, a majority of combustion occurs within the perforations 210 of the perforated flame holder 102, between the input face 212 and the output face 214. In still other instances, the inventors have noted apparent combustion occurring downstream from the output face 214 of the perforated flame holder 102, but still a majority of combustion occurred within the perforated flame holder 102 as evidenced by continued visible glow from the perforated flame holder 102 that was observed.

The perforated flame holder 102 can be configured to receive heat from the combustion reaction 302 and output a portion of the received heat as thermal radiation 304 to heat-receiving structures (e.g., furnace walls and/or radiant section working fluid tubes) in or adjacent to the combustion volume 204. As used herein, terms such as radiation, thermal radiation, radiant heat, heat radiation, etc. are to be construed as being substantially synonymous, unless further definition is provided. Specifically, such terms refer to blackbody-type radiation of electromagnetic energy, primarily at infrared wavelengths, but also at visible wavelengths owing to elevated temperature of the perforated flame holder body 208.

Referring especially to FIG. 3, the perforated flame holder 102 outputs another portion of the received heat to the fuel and oxidant mixture 206 received at the input face 212 of the perforated flame holder 102. The perforated flame holder body 208 may receive heat from the combustion reaction 302 at least in heat receiving regions 306 of perforation walls 308. Experimental evidence has suggested to the inventors that the position of the heat receiving regions 306, or at least the position corresponding to a maximum rate of receipt of heat, can vary along the length of the perforation walls 308. In some experiments, the location of maximum receipt of heat was apparently between ⅓ and ½ of the distance from the input face 212 to the output face 214 (i.e., somewhat nearer to the input face 212 than to the output face 214). The inventors contemplate that the heat receiving regions 306 may lie nearer to the output face 214 of the perforated flame holder 102 under other conditions. Most probably, there is no clearly defined edge of the heat receiving regions 306 (or for that matter, heat output regions 310, described below). For ease of understanding, the heat receiving regions 306 and the heat output regions 310 will be described as particular regions 306, 310.

The perforated flame holder body 208 can be characterized by a heat capacity. The perforated flame holder body 208 may hold thermal energy from the combustion reaction 302 in an amount corresponding to the heat capacity multiplied by temperature rise, and transfer the thermal energy from the heat receiving regions 306 to the heat output regions 310 of the perforation walls 308. Generally, the heat output regions 310 are nearer to the input face 212 than are the heat receiving regions 306. According to one interpretation, the perforated flame holder body 208 can transfer heat from the heat receiving regions 306 to the heat output regions 310 via thermal radiation, depicted graphically as 304. According to another interpretation, the perforated flame holder body 208 can transfer heat from the heat receiving regions 306 to the heat output regions 310 via heat conduction along heat conduction paths 312. The inventors contemplate that multiple heat transfer mechanisms including conduction, radiation, and possibly convection may be operative in transferring heat from the heat receiving regions 306 to the heat output regions 310. In this way, the perforated flame holder 102 may act as a heat source to maintain the combustion reaction 302, even under conditions where the combustion reaction 302 would not be stable when supported from a conventional flame holder.

The inventors believe that the perforated flame holder 102 causes the combustion reaction 302 to begin within thermal boundary layers 314 formed adjacent to the walls 308 of the perforations 210. Insofar as combustion is generally understood to include a large number of individual reactions, and since a large portion of combustion energy is released within the perforated flame holder 102, it is apparent that at least a majority of the individual reactions occur within the perforated flame holder 102. As the relatively cool fuel and oxidant mixture 206 approaches the input face 212, the flow is split into portions that respectively travel through individual perforations 210. The hot perforated flame holder body 208 transfers heat to the fluid, notably within the thermal boundary layers 314 that progressively thicken as more and more heat is transferred to the incoming fuel and oxidant mixture 206. After reaching a combustion temperature (e.g., the auto-ignition temperature of the fuel), the reactants continue to flow while a chemical ignition delay time elapses, over which time the combustion reaction 302 occurs. Accordingly, the combustion reaction 302 is shown as occurring within the thermal boundary layers 314. As flow progresses, the thermal boundary layers 314 merge at a merger point 316. Ideally, the merger point 316 lies between the input face 212 and the output face 214 that define the ends of the perforations 210. At some position along the length of a perforation 210, the combustion reaction 302 outputs more heat to the perforated flame holder body 208 than it receives from the perforated flame holder body 208. The heat is received at the heat receiving region 306, is held by the perforated flame holder body 208, and is transported to the heat output region 310 nearer to the input face 212, where the heat is transferred into the cool reactants (and any included diluent) to bring the reactants to the ignition temperature.

In an embodiment, each of the perforations 210 is characterized by a length L defined as a reaction fluid propagation path length between the input face 212 and the output face 214 of the perforated flame holder 102. As used herein, the term reaction fluid refers to matter that travels through a perforation 210. Near the input face 212, the reaction fluid includes the fuel and oxidant mixture 206 (optionally including nitrogen, flue gas, and/or other "non-reactive" species). Within the combustion reaction 302 region, the reaction fluid may include plasma associated with the combustion reaction 302, molecules of reactants and their constituent parts, any non-reactive species, reaction intermediates (including transition states), and reaction products. Near the output face 214, the reaction fluid may include reaction products and byproducts, non-reactive gas, and excess oxidant.

The plurality of perforations 210 can be each characterized by a transverse dimension D between opposing perforation walls 308. The inventors have found that stable combustion can be maintained in the perforated flame holder 102 if the length L of each perforation 210 is at least four times the transverse dimension D of the perforation 210. In other embodiments, the length L can be greater than six times the transverse dimension D. For example, experiments have been run where L is at least eight, at least twelve, at least sixteen, and at least twenty-four times the transverse dimension D. Preferably, the length L is sufficiently long for the thermal boundary layers 314 to form adjacent to the perforation walls 308 in a reaction fluid flowing through the perforations 210 to converge at the merger points 316 within the perforations 210 between the input face 212 and the output face 214 of the perforated flame holder 102. In experiments, the inventors have found L/D ratios between 12 and 48 to work well (i.e., produce low NOx, produce low CO, and maintain stable combustion).

The perforated flame holder body 208 can be configured to convey heat between adjacent perforations 210. The heat conveyed between the adjacent perforations 210 can be selected to cause heat output from the combustion reaction portion 302 in a first perforation 210 to supply heat to stabilize a combustion reaction portion 302 in an adjacent perforation 210.

Referring especially to FIG. 2, the fuel and oxidant source 202 can further include a fuel nozzle 218, configured to output the fuel, and an oxidant source 220 configured to output a fluid including the oxidant. For example, the fuel nozzle 218 can be configured to output pure fuel. The oxidant source 220 can be configured to output combustion air carrying oxygen, and optionally, flue gas.

The perforated flame holder 102 can be held by a perforated flame holder support structure 222 configured to hold the perforated flame holder 102 at a dilution distance $D_O$ away from the fuel nozzle 218. The fuel nozzle 218 can be configured to emit a fuel jet selected to entrain the oxidant to form the fuel and oxidant mixture 206 as the fuel jet and the oxidant travel along a path to the perforated flame holder 102 through the dilution distance $D_O$ between the fuel nozzle 218 and the perforated flame holder 102. Additionally or alternatively (particularly when a blower is used to deliver the oxidant contained in the combustion air), the oxidant or combustion air source 220 can be configured to entrain the fuel and the fuel and the oxidant travel through the dilution distance $D_O$. In some embodiments, a flue gas recirculation path 224 can be provided. Additionally or alternatively, the fuel nozzle 218 can be configured to emit a fuel jet selected to entrain the oxidant and to entrain flue gas as the fuel jet travels through the dilution distance $D_O$ between the fuel nozzle 218 and the input face 212 of the perforated flame holder 102.

The fuel nozzle 218 can be configured to emit the fuel through one or more fuel orifices 226 having an inside diameter dimension that is referred to as "nozzle diameter." The perforated flame holder support structure 222 can support the perforated flame holder 102 to receive the fuel and oxidant mixture 206 at the distance $D_O$ away from the fuel nozzle 218 greater than 20 times the nozzle diameter. In another embodiment, the perforated flame holder 102 is disposed to receive the fuel and oxidant mixture 206 at the distance $D_O$ away from the fuel nozzle 218 between 100 times and 1100 times the nozzle diameter. Preferably, the perforated flame holder support structure 222 is configured to hold the perforated flame holder 102 at a distance about 200 times or more of the nozzle diameter away from the fuel nozzle 218. When the fuel and oxidant mixture 206 travels about 200 times the nozzle diameter or more, the fuel and oxidant mixture 206 is sufficiently homogenized to cause the combustion reaction 302 to produce minimal NOx.

The fuel and oxidant source 202 can alternatively include a premix fuel and oxidant source, according to an embodiment. A premix fuel and oxidant source can include a premix chamber (not shown), a fuel nozzle configured to output fuel into the premix chamber, and an oxidant (e.g., combustion air) channel configured to output the oxidant into the premix chamber. A flame arrestor can be disposed between the premix fuel and oxidant source and the perforated flame holder 102 and be configured to prevent flame flashback into the premix fuel and oxidant source.

The oxidant source 220, whether configured for entrainment in the combustion volume 204 or for premixing, can include a blower configured to force the oxidant through the fuel and oxidant source 202.

The perforated flame holder support structure 222 can be configured to support the perforated flame holder 102 from a floor or wall (not shown) of the combustion volume 204, for example. In another embodiment, the perforated flame holder support structure 222 supports the perforated flame holder 102 from the fuel and oxidant source 202. Alternatively, the perforated flame holder support structure 222 can suspend the perforated flame holder 102 from an overhead structure (such as a flue, in the case of an up-fired system). The perforated flame holder support structure 222 can support the perforated flame holder 102 in various orientations and directions.

The perforated flame holder 102 can include a single perforated flame holder body 208. In another embodiment, the perforated flame holder 102 can include a plurality of adjacent perforated flame holder sections that collectively provide a tiled perforated flame holder 102.

The perforated flame holder support structure 222 can be configured to support the plurality of perforated flame holder sections. The perforated flame holder support structure 222 can include a metal superalloy, a cementatious, and/or ceramic refractory material. In an embodiment, the plurality of adjacent perforated flame holder sections can be joined with a fiber reinforced refractory cement.

The perforated flame holder 102 can have a width dimension W between opposite sides of the peripheral surface 216 at least twice a thickness dimension T between the input face 212 and the output face 214. In another embodiment, the perforated flame holder 102 can have a width dimension W between opposite sides of the peripheral surface 216 at least three times, at least six times, or at least nine times the thickness dimension T between the input face 212 and the output face 214 of the perforated flame holder 102.

In an embodiment, the perforated flame holder 102 can have a width dimension W less than a width of the combustion volume 204. This can allow the flue gas recirculation path 224 from above to below the perforated flame holder 102 to lie between the peripheral surface 216 of the perforated flame holder 102 and the combustion volume wall (not shown).

Referring again to both FIGS. 2 and 3, the perforations 210 can be of various shapes. In an embodiment, the perforations 210 can include elongated squares, each having a transverse dimension D between opposing sides of the squares. In another embodiment, the perforations 210 can include elongated hexagons, each having a transverse dimension D between opposing sides of the hexagons. In yet another embodiment, the perforations 210 can include hollow cylinders, each having a transverse dimension D corresponding to a diameter of the cylinder. In another embodiment, the perforations 210 can include truncated cones or truncated pyramids (e.g., frustums), each having a transverse dimension D radially symmetric relative to a length axis that extends from the input face 212 to the output face 214. In some embodiments, the perforations 210 can each have a lateral dimension D equal to or greater than a quenching distance of the flame based on standard reference conditions. Alternatively, the perforations 210 may have lateral dimension D less then than a standard reference quenching distance.

In one range of embodiments, each of the plurality of perforations 210 has a lateral dimension D between 0.05 inch and 1.0 inch. Preferably, each of the plurality of perforations 210 has a lateral dimension D between 0.1 inch and 0.5 inch. For example, the plurality of perforations 210 can each have a lateral dimension D of about 0.2 to 0.4 inch.

The void fraction of a perforated flame holder 102 is defined as the total volume of all perforations 210 in a section of the perforated flame holder 102 divided by a total volume of the perforated flame holder 102 including the perforated flame holder body 208 and the perforations 210. The perforated flame holder 102 should have a void fraction between 0.10 and 0.90. In an embodiment, the perforated flame holder 102 can have a void fraction between 0.30 and 0.80. In another embodiment, the perforated flame holder 102 can have a void fraction of about 0.70. Using a void fraction of about 0.70 was found to be especially effective for producing very low NOx.

The perforated flame holder 102 can be formed from a fiber reinforced cast refractory material and/or a refractory material such as an aluminum silicate material. For example, the perforated flame holder 102 can be formed to include mullite or cordierite. Additionally or alternatively, the perforated flame holder body 208 can include a metal superalloy such as Inconel or Hastelloy. The perforated flame holder body 208 can define a honeycomb. Honeycomb is an industrial term of art that need not strictly refer to a hexagonal cross section and most usually includes cells of square cross section. Honeycombs of other cross sectional areas are also known.

The inventors have found that the perforated flame holder 102 can be formed from VERSAGRID® ceramic honeycomb, available from Applied Ceramics, Inc. of Doraville, South Carolina.

The perforations 210 can be parallel to one another and normal to the input and the output faces 212, 214. In another embodiment, the perforations 210 can be parallel to one another and formed at an angle relative to the input and the output faces 212, 214. In another embodiment, the perforations 210 can be non-parallel to one another. In another embodiment, the perforations 210 can be non-parallel to one another and non-intersecting. In another embodiment, the perforations 210 can be intersecting. The perforated flame holder body 208 can be one piece or can be formed from a plurality of sections.

In another embodiment, which is not necessarily preferred, the perforated flame holder 102 may be formed from reticulated ceramic material. The term "reticulated" refers to a netlike structure. Reticulated ceramic material is often made by dissolving a slurry into a sponge of specified porosity, allowing the slurry to harden, and burning away the sponge and curing the ceramic.

In another embodiment, which is not necessarily preferred, the perforated flame holder 102 may be formed from a ceramic material that has been punched, bored or cast to create channels.

In another embodiment, the perforated flame holder 102 can include a plurality of tubes or pipes bundled together. The plurality of perforations 210 can include hollow cylinders and can optionally also include interstitial spaces between the bundled tubes. In an embodiment, the plurality of tubes can include ceramic tubes. Refractory cement can be included between the tubes and configured to adhere the tubes together. In another embodiment, the plurality of tubes can include metal (e.g., superalloy) tubes. The plurality of tubes can be held together by a metal tension member circumferential to the plurality of tubes and arranged to hold the plurality of tubes together. The metal tension member can include stainless steel, a superalloy metal wire, and/or a superalloy metal band.

The perforated flame holder body 208 can alternatively include stacked perforated sheets of material, each sheet having openings that connect with openings of subjacent and superjacent sheets. The perforated sheets can include perforated metal sheets, ceramic sheets and/or expanded sheets. In another embodiment, the perforated flame holder body 208 can include discontinuous packing bodies such that the perforations 210 are formed in the interstitial spaces between the discontinuous packing bodies. In one example, the discontinuous packing bodies include structured packing shapes. In another example, the discontinuous packing bodies include random packing shapes. For example, the discontinuous packing bodies can include ceramic Raschig ring, ceramic Berl saddles, ceramic Intalox saddles, and/or metal rings or other shapes (e.g., Super Raschig Rings) that may be held together by a metal cage.

The inventors contemplate various explanations for why burner systems 200 including the perforated flame holder 102 provide such clean combustion.

According to an embodiment, the perforated flame holder 102 may act as a heat source to maintain the combustion reaction 302 even under conditions where the combustion reaction 302 would not be stable when supported by a conventional flame holder. This capability can be leveraged to support combustion using a leaner fuel-to-oxidant mixture than is typically feasible. Thus, according to an embodiment, at the point where the fuel stream 206 contacts the input face 212 of the perforated flame holder 102, an average fuel-to-oxidant ratio of the fuel stream 206 is below a (conventional) lower combustion limit of the fuel component of the fuel stream 206-lower combustion limit defines the lowest concentration of fuel at which a fuel and oxidant mixture 206 will burn when exposed to a momentary ignition source under normal atmospheric pressure and an ambient temperature of 25° C. (77° F.).

The perforated flame holder 102 and systems including the perforated flame holder 102 described herein were found to provide substantially complete combustion of CO (single digit ppm down to undetectable, depending on experimental conditions), while supporting low NOx. According to one interpretation, such a performance can be achieved due to a sufficient mixing used to lower peak flame temperatures (among other strategies). Flame temperatures tend to peak under slightly rich conditions, which can be evident in any diffusion flame that is insufficiently mixed. By sufficiently mixing, a homogenous and slightly lean mixture can be achieved prior to combustion. This combination can result in reduced flame temperatures, and thus reduced NOx formation. In one embodiment, "slightly lean" may refer to 3% $O_2$, i.e., an equivalence ratio of ~0.87. Use of even leaner mixtures is possible, but may result in elevated levels of $O_2$. Moreover, the inventors believe the perforation walls 308 may act as a heat sink for the combustion fluid. This effect may alternatively or additionally reduce combustion temperatures and lower NOx.

According to another interpretation, production of NOx can be reduced if the combustion reaction 302 occurs over a very short duration of time. Rapid combustion causes the reactants (including oxygen and entrained nitrogen) to be exposed to NOx-formation temperature for a time too short for NOx formation kinetics to cause significant production of NOx. The time required for the reactants to pass through the perforated flame holder 102 is very short compared to a conventional flame. The low NOx production associated with perforated flame holder combustion may thus be related to the short duration of time required for the reactants (and entrained nitrogen) to pass through the perforated flame holder 102.

Figure 4:
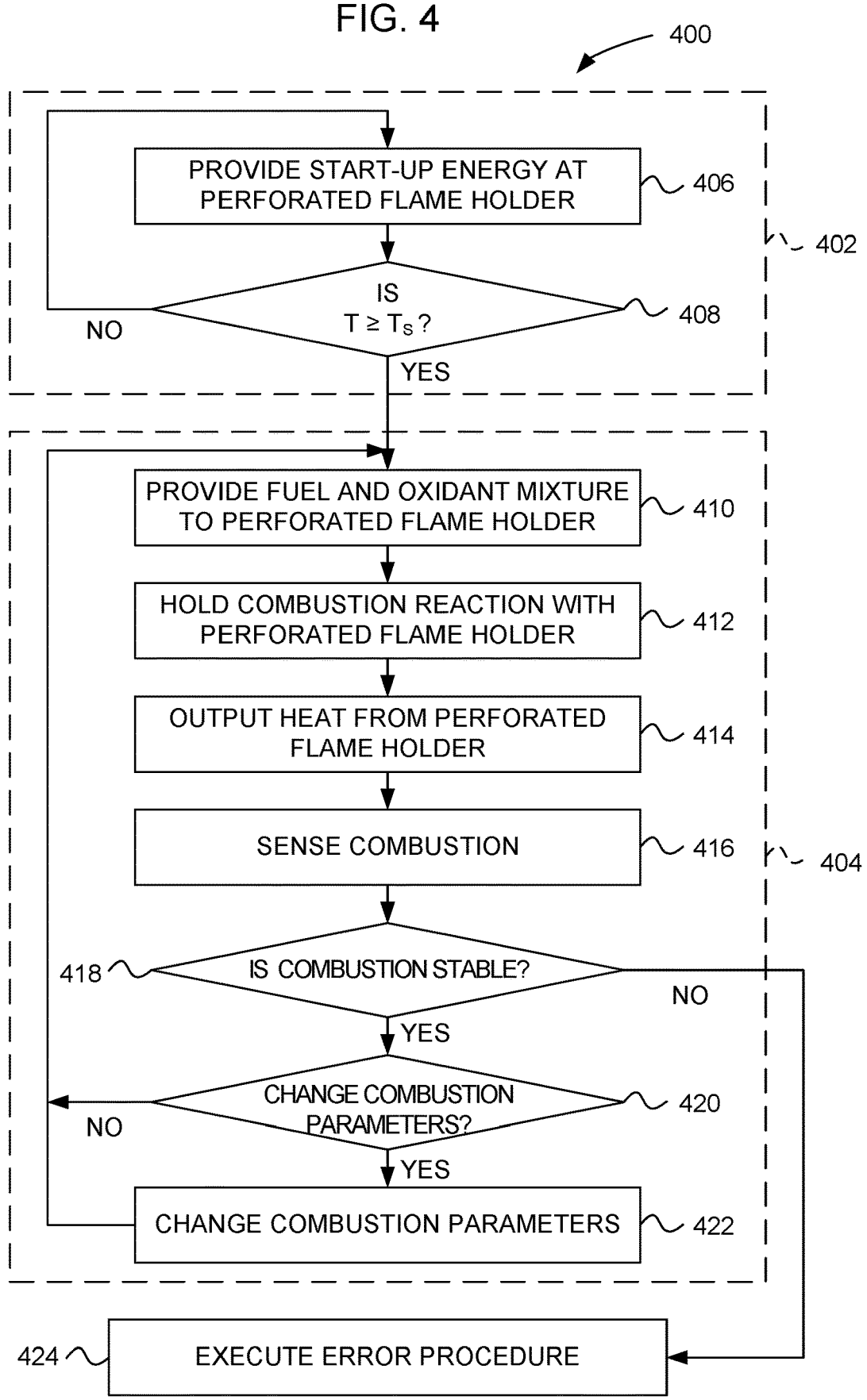
FIG. 4 is a flow chart showing a method for operating a burner system including the perforated flame holder of FIGS. 1A-B, 2, and 3, according to an embodiment.

FIG. 4 is a flow chart showing a method 400 for operating a burner system including the perforated flame holder shown and described herein. To operate a burner system including a perforated flame holder, the perforated flame holder is first heated to a temperature sufficient to maintain combustion of the fuel and oxidant mixture.

According to a simplified description, the method 400 begins with step 402, wherein the perforated flame holder is preheated to a start-up temperature, $T_S$. After the perforated flame holder is raised to the start-up temperature, the method proceeds to step 404, wherein the fuel and oxidant are provided to the perforated flame holder and combustion is held by the perforated flame holder.

According to a more detailed description, step 402 begins with step 406, wherein start-up energy is provided at the perforated flame holder. Simultaneously or following providing start-up energy, a decision step 408 determines whether the temperature T of the perforated flame holder is at or above the start-up temperature, $T_S$. As long as the temperature of the perforated flame holder is below its start-up temperature, the method loops between steps 406 and 408 within the preheat step 402. In decision step 408, if the temperature T of at least a predetermined portion of the perforated flame holder is greater than or equal to the start-up temperature, the method 400 proceeds to overall step 404, wherein fuel and oxidant is supplied to and combustion is held by the perforated flame holder.

Step 404 may be broken down into several discrete steps, at least some of which may occur simultaneously.

Proceeding from decision step 408, a fuel and oxidant mixture is provided to the perforated flame holder, as shown in step 410. The fuel and oxidant may be provided by a fuel and oxidant source that includes a separate fuel nozzle and oxidant (e.g., combustion air) source, for example. In this approach, the fuel and oxidant are output in one or more directions selected to cause the fuel and oxidant mixture to be received by the input face of the perforated flame holder. The fuel may entrain the combustion air (or alternatively, the combustion air may dilute the fuel) to provide a fuel and oxidant mixture at the input face of the perforated flame holder at a fuel dilution selected for a stable combustion reaction that can be held within the perforations of the perforated flame holder.

Proceeding to step 412, the combustion reaction is held by the perforated flame holder.

In step 414, heat may be output from the perforated flame holder. The heat output from the perforated flame holder may be used to power an industrial process, heat a working fluid, generate electricity, or provide motive power, for example.

In optional step 416, the presence of combustion may be sensed. Various sensing approaches have been used and are contemplated by the inventors. Generally, combustion held by the perforated flame holder is very stable and no unusual sensing requirement is placed on the system. Combustion sensing may be performed using an infrared sensor, a video sensor, an ultraviolet sensor, a charged species sensor, thermocouple, thermopile, flame rod, and/or other combustion sensing apparatuses. In an additional or alternative variant of step 416, a pilot flame or other ignition source may be provided to cause ignition of the fuel and oxidant mixture in the event combustion is lost at the perforated flame holder.

Proceeding to decision step 418, if combustion is sensed not to be stable, the method 400 may exit to step 424, wherein an error procedure is executed. For example, the error procedure may include turning off fuel flow, re-executing the preheating step 402, outputting an alarm signal, igniting a stand-by combustion system, or other steps. If, in decision step 418, combustion in the perforated flame holder is determined to be stable, the method 400 proceeds to decision step 420, wherein it is determined if combustion parameters should be changed. If no combustion parameters are to be changed, the method loops (within step 404) back to step 410, and the combustion process continues. If a change in combustion parameters is indicated, the method 400 proceeds to step 422, wherein the combustion parameter change is executed. After changing the combustion parameter(s), the method loops (within step 404) back to step 410, and combustion continues.

Combustion parameters may be scheduled to be changed, for example, if a change in heat demand is encountered. For example, if less heat is required (e.g., due to decreased electricity demand, decreased motive power requirement, or lower industrial process throughput), the fuel and oxidant flow rate may be decreased in step 422. Conversely, if heat demand is increased, then fuel and oxidant flow may be increased. Additionally or alternatively, if the combustion system is in a start-up mode, then fuel and oxidant flow may be gradually increased to the perforated flame holder over one or more iterations of the loop within step 404.

Referring again to FIG. 2, the burner system 200 includes a heater 228 operatively coupled to the perforated flame holder 102. As described in conjunction with FIGS. 3 and 4, the perforated flame holder 102 operates by outputting heat to the incoming fuel and oxidant mixture 206. After combustion is established, this heat is provided by the combustion reaction 302; but before combustion is established, the heat is provided by the heater 228.

Various heating apparatuses have been used and are contemplated by the inventors. In some embodiments, the heater 228 can include a flame holder configured to support a flame disposed to heat the perforated flame holder 102. The fuel and oxidant source 202 can include a fuel nozzle 218 configured to emit a fuel stream 206 and an oxidant source 220 configured to output oxidant (e.g., combustion air) adjacent to the fuel stream 206. The fuel nozzle 218 and the oxidant source 220 can be configured to output the fuel stream 206 to be progressively diluted by the oxidant (e.g., combustion air). The perforated flame holder 102 can be disposed to receive a diluted fuel and oxidant mixture 206 that supports a combustion reaction 302 that is stabilized by the perforated flame holder 102 when the perforated flame holder 102 is at an operating temperature. A start-up flame holder, in contrast, can be configured to support a start-up flame at a location corresponding to a relatively unmixed fuel and oxidant mixture that is stable without stabilization provided by the heated perforated flame holder 102.

The burner system 200 can further include a controller 118 operatively coupled to the heater 228 and to a data interface 232. For example, the controller 118 can be configured to control a start-up flame holder actuator configured to cause the start-up flame holder to hold the start-up flame when the perforated flame holder 102 needs to be pre-heated and to not hold the start-up flame when the perforated flame holder 102 is at an operating temperature (e.g., when $T \; T_S$).

Various approaches for actuating a start-up flame are contemplated. In one embodiment, the start-up flame holder includes a mechanically-actuated bluff body configured to be actuated to intercept the fuel and oxidant mixture 206 to cause heat-recycling and/or stabilizing vortices and thereby hold a start-up flame; or to be actuated to not intercept the fuel and oxidant mixture 206 to cause the fuel and oxidant mixture 206 to proceed to the perforated flame holder 102. In another embodiment, a fuel control valve, blower, and/or damper may be used to select a fuel and oxidant mixture 206 flow rate that is sufficiently low for a start-up flame to be jet-stabilized; and upon reaching a perforated flame holder 102 operating temperature, the flow rate may be increased to "blow out" the start-up flame. In another embodiment, the heater 228 may include an electrical power supply operatively coupled to the controller 118 and configured to apply an electrical charge or voltage to the fuel and oxidant mixture 206. An electrically conductive start-up flame holder may be selectively coupled to a voltage ground or other voltage selected to attract the electrical charge in the fuel and oxidant mixture 206. The attraction of the electrical charge was found by the inventors to cause a start-up flame to be held by the electrically conductive start-up flame holder.

In another embodiment, the heater 228 may include an electrical resistance heater configured to output heat to the perforated flame holder 102 and/or to the fuel and oxidant mixture 206. The electrical resistance heater can be configured to heat up the perforated flame holder 102 to an operating temperature. The heater 228 can further include a power supply and a switch operable, under control of the controller 118, to selectively couple the power supply to the electrical resistance heater 228.

An electrical resistance heater 228 can be formed in various ways. For example, the electrical resistance heater 228 can be formed from KANTHAL® wire (available from Sandvik Materials Technology division of Sandvik AB of Hallstahammar, Sweden) threaded through at least a portion of the perforations 210 defined by the perforated flame holder body 208. Alternatively, the heater 228 can include an inductive heater, a high-energy beam heater (e.g. microwave or laser), a frictional heater, electro-resistive ceramic coatings, or other types of heating technologies.

Other forms of start-up apparatuses are contemplated. For example, the heater 228 can include an electrical discharge igniter or hot surface igniter configured to output a pulsed ignition to the oxidant and fuel. Additionally or alternatively, a start-up apparatus can include a pilot flame apparatus disposed to ignite the fuel and oxidant mixture 206 that would otherwise enter the perforated flame holder 102. The electrical discharge igniter, hot surface igniter, and/or pilot flame apparatus can be operatively coupled to the controller 118, which can cause the electrical discharge igniter or pilot flame apparatus to maintain combustion of the fuel and oxidant mixture 206 in or upstream from the perforated flame holder 102 before the perforated flame holder 102 is heated sufficiently to maintain combustion.

The burner system 200 can further include a sensor 234 operatively coupled to the controller 118. The sensor 234 can include a heat sensor configured to detect infrared radiation or a temperature of the perforated flame holder 102. The control circuit 118 can be configured to control the heater 228 responsive to input from the sensor 234. Optionally, a fuel control valve 236 can be operatively coupled to the controller 118 and configured to control a flow of the fuel to the fuel and oxidant source 202. Additionally or alternatively, an oxidant blower or damper 238 can be operatively coupled to the controller 118 and configured to control flow of the oxidant (or combustion air).

The sensor 234 can further include a combustion sensor operatively coupled to the control circuit 118, the combustion sensor being configured to detect a temperature, video image, and/or spectral characteristic of a combustion reaction 302 held by the perforated flame holder 102. The fuel control valve 236 can be configured to control a flow of the fuel from a fuel source to the fuel and oxidant source 202. The controller 118 can be configured to control the fuel control valve 236 responsive to input from the combustion sensor 234. The controller 118 can be configured to control the fuel control valve 236 and/or the oxidant blower or damper 238 to control a preheat flame type of heater 228 to heat the perforated flame holder 102 to an operating temperature. The controller 118 can similarly control the fuel control valve 236 and/or the oxidant blower or damper 238 to change the fuel and oxidant mixture 206 flow responsive to a heat demand change received as data via the data interface 232.

Figure 5A:
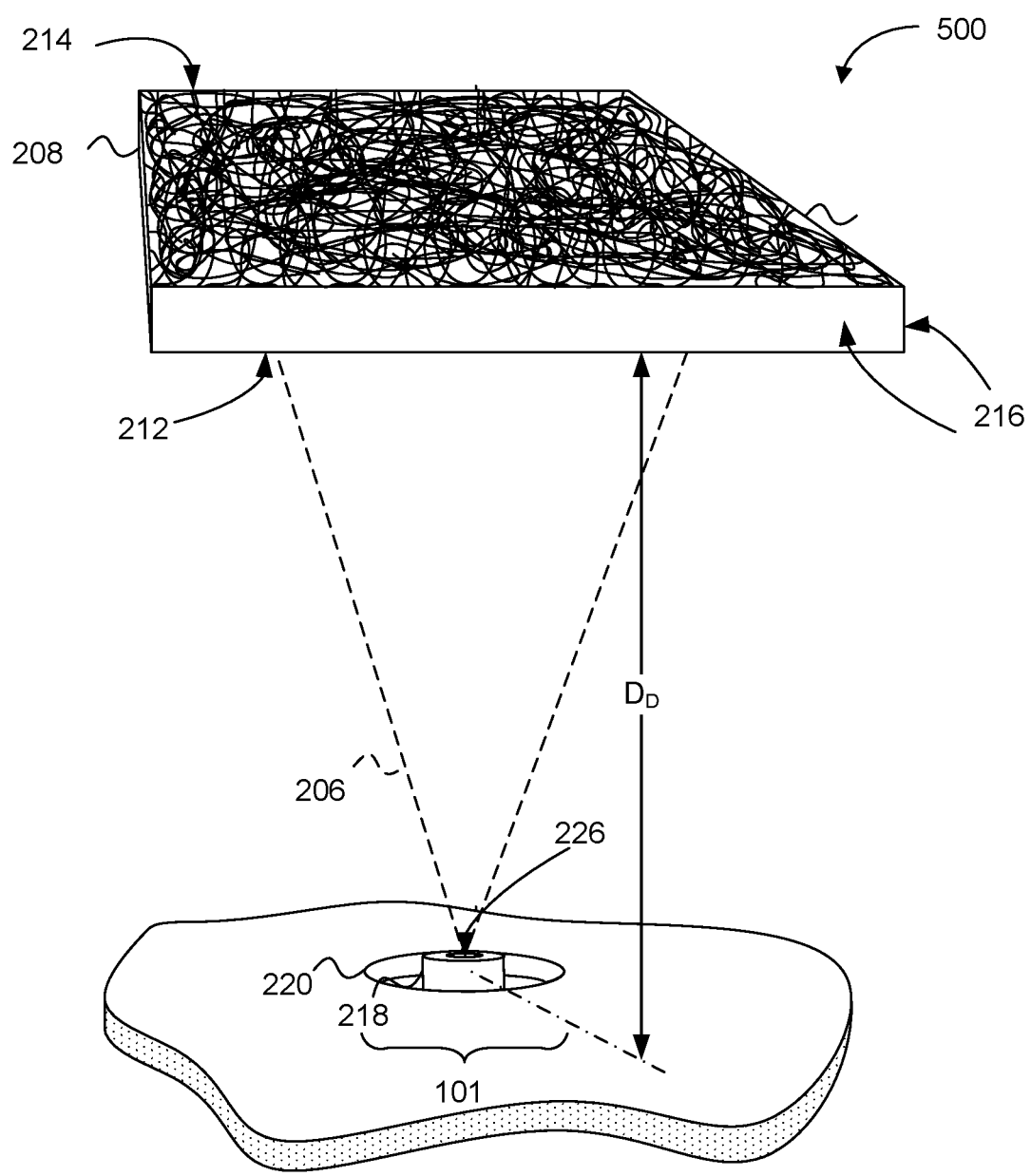
FIG. 5A is a simplified perspective view of a combustion system, including another alternative perforated flame holder, according to an embodiment.
Figure 5B:
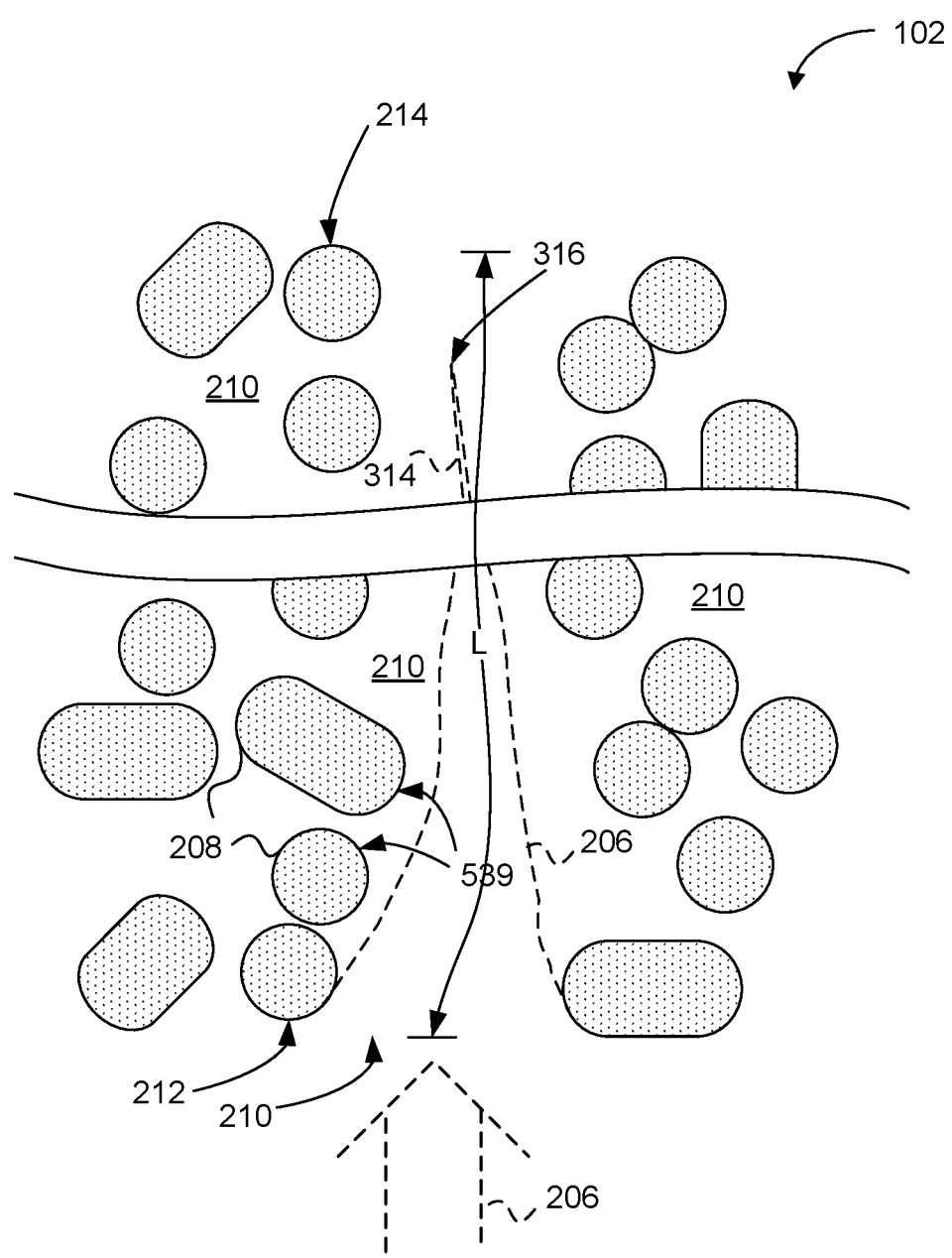
FIG. 5B is a simplified side sectional diagram of a portion of the reticulated ceramic perforated flame holder of FIG. 5A, according to an embodiment.

FIG. 5A is a simplified perspective view of a combustion system 500, including another alternative perforated flame holder 102, according to an embodiment. The perforated flame holder 102 is a reticulated ceramic perforated flame holder, according to an embodiment. FIG. 5B is a simplified side sectional diagram of a portion of the reticulated ceramic perforated flame holder 102 of FIG. 5A, according to an embodiment. The perforated flame holder 102 of FIGS. 5A, 5B can be implemented in the various combustion systems described herein, according to an embodiment. The perforated flame holder 102 is configured to support a combustion reaction (e.g., combustion reaction 302 of FIG. 3) of the fuel and oxidant mixture 206 received from the fuel and oxidant source 202 at least partially within the perforated flame holder 102. According to an embodiment, the perforated flame holder 102 can be configured to support a combustion reaction (e.g., combustion reaction 302 of FIG. 3) of the fuel and oxidant mixture 206 upstream, downstream, within, and adjacent to the reticulated ceramic perforated flame holder 102.

According to an embodiment, the perforated flame holder body 208 can include reticulated fibers 539. The reticulated fibers 539 can define branching perforations 210 that weave around and through the reticulated fibers 539. According to an embodiment, the perforations 210 are formed as passages between the reticulated fibers 539.

According to an embodiment, the reticulated fibers 539 are formed as a reticulated ceramic foam. According to an embodiment, the reticulated fibers 539 are formed using a reticulated polymer foam as a template. According to an embodiment, the reticulated fibers 539 can include alumina silicate. According to an embodiment, the reticulated fibers 539 can be formed from extruded mullite or cordierite. According to an embodiment, the reticulated fibers 539 can include Zirconia. According to an embodiment, the reticulated fibers 539 can include silicon carbide.

The term "reticulated fibers" refers to a netlike structure. According to an embodiment, the reticulated fibers 539 are formed from an extruded ceramic material. In reticulated fiber embodiments, the interaction between the fuel and oxidant mixture 206, the combustion reaction, and heat transfer to and from the perforated flame holder body 208 can function similarly to the embodiment shown and described above with respect to FIGS. 2-4. One difference in activity is a mixing between perforations 210, because the reticulated fibers 539 form a discontinuous perforated flame holder body 208 that allows flow back and forth between neighboring perforations 210.

According to an embodiment, the reticulated fiber 539 network is sufficiently open for downstream reticulated fibers 539 to emit radiation for receipt by upstream reticulated fibers 539 for the purpose of heating the upstream reticulated fibers 539 sufficiently to maintain combustion of a fuel and oxidant mixture 206. Compared to a continuous perforated flame holder body 208, heat conduction paths (such as heat conduction paths 312 in FIG. 3) between reticulated fibers 539 are reduced due to separation of the reticulated fibers 539. This may cause relatively more heat to be transferred from a heat-receiving region or area (such as heat receiving region 306 in FIG. 3) to a heat-output region or area (such as heat-output region 310 of FIG. 3) of the reticulated fibers 539 via thermal radiation (shown as element 304 in FIG. 3).

According to an embodiment, individual perforations 210 may extend between an input face 212 to an output face 214 of the perforated flame holder 102. Perforations 210 may have varying lengths L. According to an embodiment, because the perforations 210 branch into and out of each other, individual perforations 210 are not clearly defined by a length L.

According to an embodiment, the perforated flame holder 102 is configured to support or hold a combustion reaction (see element 302 of FIG. 3) or a flame at least partially between the input face 212 and the output face 214. According to an embodiment, the input face 212 corresponds to a surface of the perforated flame holder 102 proximal to the fuel nozzle 218 or to a surface that first receives fuel. According to an embodiment, the input face 212 corresponds to an extent of the reticulated fibers 539 proximal to the fuel nozzle 218. According to an embodiment, the output face 214 corresponds to a surface distal to the fuel nozzle 218 or opposite the input face 212. According to an embodiment, the input face 212 corresponds to an extent of the reticulated fibers 539 distal to the fuel nozzle 218 or opposite to the input face 212.

According to an embodiment, the formation of thermal boundary layers 314, transfer of heat between the perforated reaction holder body 208 and the gases flowing through the perforations 210, a characteristic perforation width dimension D, and the length L can each be regarded as related to an average or overall path through the perforated flame holder 102. In other words, the dimension D can be determined as a root-mean-square of individual Dn values determined at each point along a flow path. Similarly, the length L can be a length that includes length contributed by tortuosity of the flow path, which may be somewhat longer than a straight line distance $T_{RH}$ from the input face 212 to the output face 214 through the perforated flame holder 102. According to an embodiment, the void fraction (expressed as (total perforated flame holder 102 volume−reticulated fiber 539 volume)/total volume)) is about 70%.

According to an embodiment, the reticulated ceramic perforated flame holder 102 is a tile about 1"×4"×4". According to an embodiment, the reticulated ceramic perforated flame holder 102 includes about 10 pores per square inch of surface area. Other materials and dimensions can also be used for a reticulated ceramic perforated flame holder 102 in accordance with principles of the present disclosure.

According to an embodiment, the reticulated ceramic perforated flame holder 102 can include shapes and dimensions other than those described herein. For example, the perforated flame holder 102 can include reticulated ceramic tiles that are larger or smaller than the dimensions set forth above. Additionally, the reticulated ceramic perforated flame holder 102 can include shapes other than generally cuboid shapes.

According to an embodiment, the reticulated ceramic perforated flame holder 102 can include multiple reticulated ceramic tiles. The multiple reticulated ceramic tiles can be joined together such that each ceramic tile is in direct contact with one or more adjacent reticulated ceramic tiles. The multiple reticulated ceramic tiles can collectively form a single perforated flame holder 102. Alternatively, each reticulated ceramic tile can be considered a distinct perforated flame holder 102.

Figure 6:
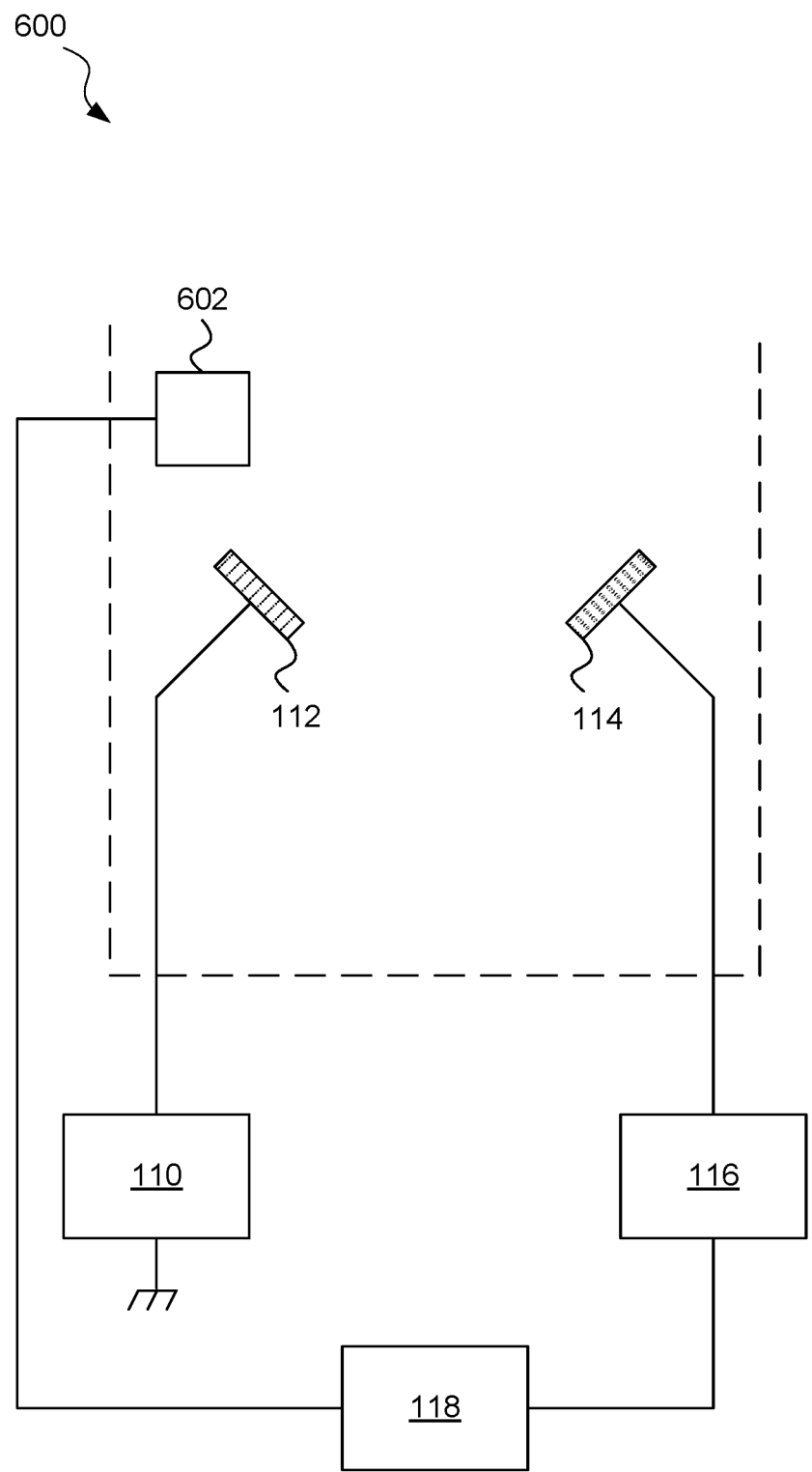
FIG. 6 is a simplified diagram of a combustion system, according to an embodiment.

FIG. 6 is a simplified diagram of a combustion system 600, according to an embodiment. The combustion system 600 may include a sensor 602 operatively coupled to the control circuit 118. The sensor 602 may be configured to sense one or more of pressure and temperature.

Figure 7:
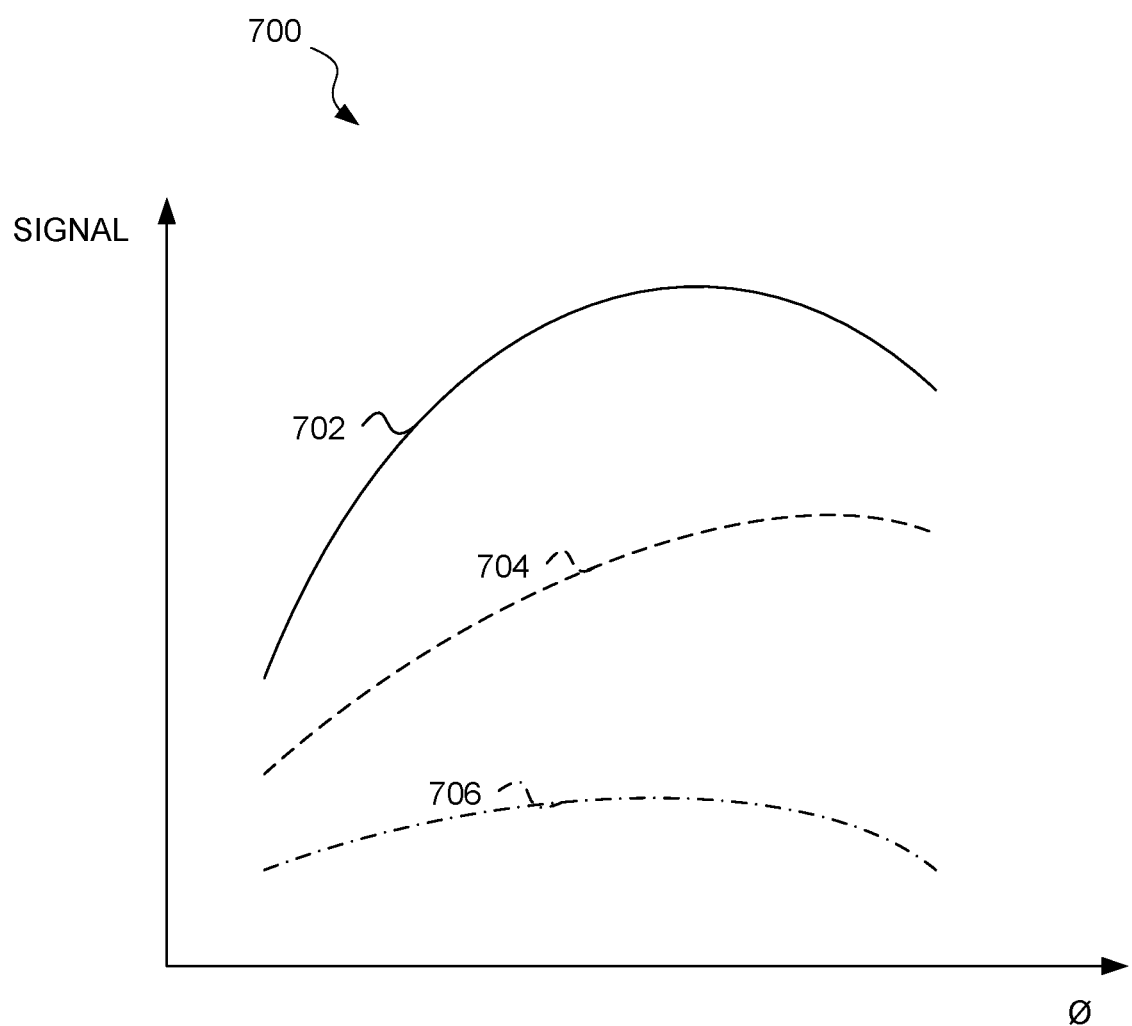
FIG. 7 is an idealized graph showing how a received signal varies with the fuel-oxidant equivalence ratio at each of three ambient conditions, according to an embodiment.

FIG. 7 is an idealized graph 700 showing how the received signal varies with the fuel-oxidant equivalence ratio at each of three ambient conditions 702, 704, 706. In one embodiment, temperature is held constant, and each curve 702, 704, 706 represents a different pressure. In another embodiment, pressure is held constant, and each curve 702, 704, 706 represents a different temperature. In another embodiment, each curve 702, 704, 706 represents a different pressure and temperature combination.

Referring to FIG. 7, the control circuit 118 may be configured to determine the fuel-oxidant equivalence ratio as a function of a value of the received signal in combination with a value of sensed temperature and/or pressure, according to an embodiment.

Figure 8:
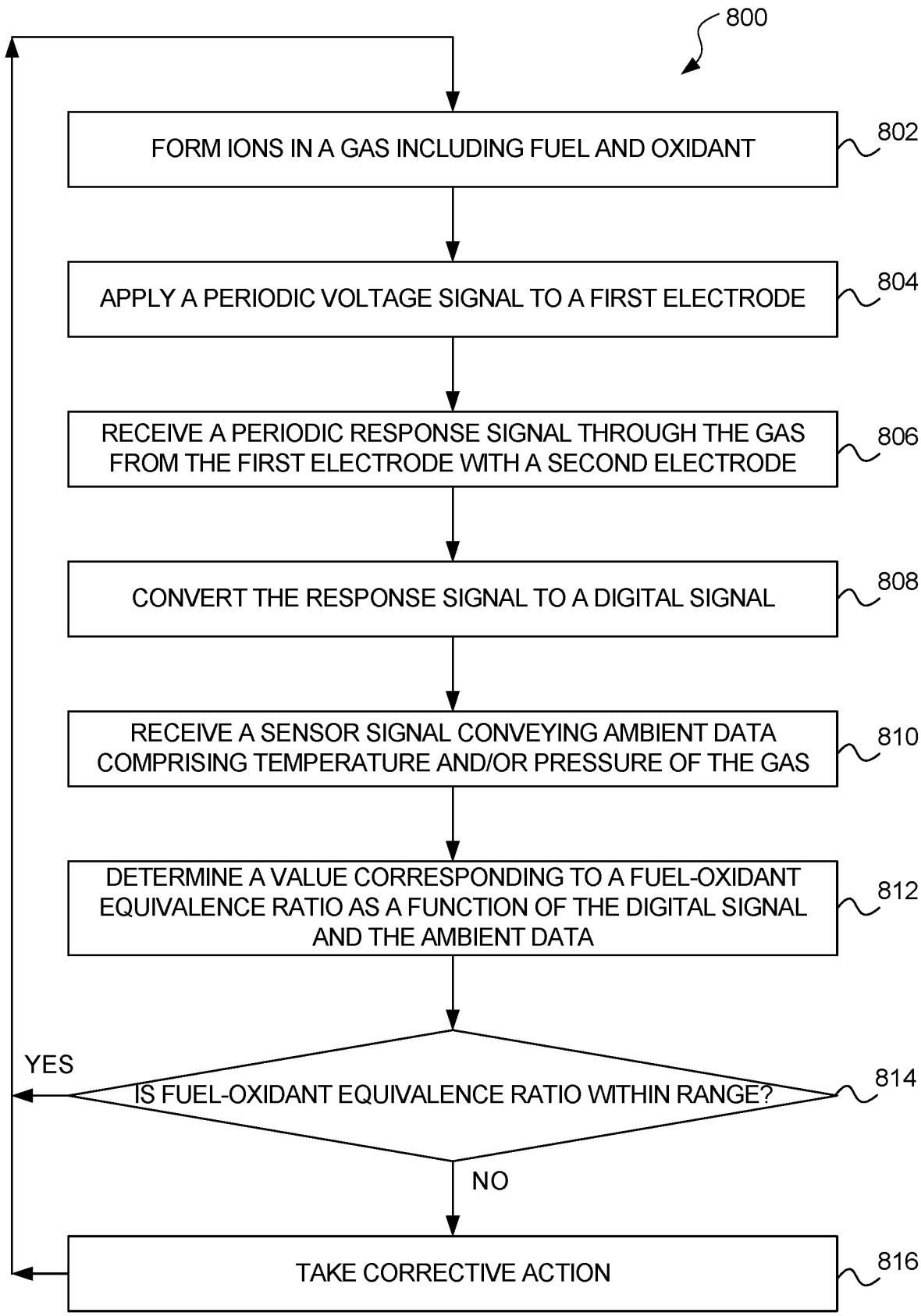
FIG. 8 is a flow chart showing a method for measuring a fuel-oxidant equivalence ratio, according to an embodiment.

FIG. 8 is a flow chart showing a method 800 for measuring a fuel-oxidant equivalence ratio, according to an embodiment.

According to an embodiment, the method 800 includes step 802, wherein ion formation is caused in a gas including fuel and oxidant. In step 804, a periodic voltage signal is applied to a first electrode adjacent to the gas. In step 806, a periodic response signal is operatively coupled through the gas to a second electrode. A periodic response signal may be produced according to a response of the ions to the periodic voltage signal, according to an embodiment. The method 800 may include converting the periodic response signal to a corresponding digital signal in step 808. In step 810, a sensor signal corresponding to an independent parameter of the gas is received, according to an embodiment. The method 800 may include step 812, which includes applying the digital signal and the sensor signal as arguments for a function and determining a value of the function corresponding to the fuel-oxidant equivalence ratio, according to an embodiment.

According to an embodiment, the method 800 further may include holding a pressure of the gas constant. In an embodiment, receiving the sensor signal in step 810 may include receiving a signal corresponding to a temperature of the gas. Additionally or alternatively, the method 800 may include holding a temperature of the gas constant and, in step 810, receiving the sensor signal corresponding to a pressure of the gas. Additionally or alternatively, receiving the sensor signal in step 810 may include receiving a temperature signal corresponding to a temperature of the gas and receiving a pressure signal corresponding to a pressure of the gas.

According to an embodiment, causing ion formation in the gas in step 802 may include operating an ionizer. Various electrode configurations and types are contemplated. According to an embodiment, operating the ionizer may include applying a voltage to a corona electrode and/or a dielectric barrier layer electrode.

According to an embodiment, the corona electrode may be disposed in a gas volume in which the first and the second electrodes may be disposed.

Additionally or alternatively, causing ion formation in the gas in step 802 may include operating an ionizer in a removed gas volume and conveying at least a portion of the ions from the removed gas volume to a gas volume in which the first and the second electrodes are disposed.

According to an embodiment, the method 800 may include determining whether a fuel-oxidant equivalence ratio is within a combustion limit of the fuel in step 814, and actuating a valve to change the fuel-air equivalence ratio to a ratio outside the combustion limit of the fuel, in step 816.

According to an embodiment, actuating the valve may include purging the gas with an inert gas (such as nitrogen or carbon dioxide).

According to an embodiment, the fuel may include kerosene.

According to an embodiment, the method 800 further may include isolating the ions inside a grounded screen forming a flame arrestor.

Additionally or alternatively, causing ion formation in the gas in step 802 may include supporting a combustion reaction in the gas.

According to an embodiment, the method 800 further may include outputting the fuel and the air toward a perforated flame holder. Causing ion formation in the gas in step 802 may include supporting the combustion reaction at least partially within the perforated flame holder, according to an embodiment.

According to an embodiment, the first electrode may be disposed to output the periodic voltage signal toward the perforated flame holder with the second electrode disposed to receive the periodic response signal at least partially through the perforated flame holder.

According to an embodiment, the method 800 further may include determining whether a fuel-air equivalence ratio is within range in step 814, and in step 816, taking corrective action if the fuel-air equivalence ratio is not within the range.

According to an embodiment, the method 800 further may include, in step 814, determining whether a fuel-air equivalence ratio is at or near a combustion limit of the fuel and, in step 816, actuating a valve to change the fuel-air equivalence ratio to a value nearer the center of the combustion limits.

According to an embodiment, determining whether the fuel-air equivalence ratio is near the combustion limit in step 814 may include determining whether the equivalence ratio is outside the combustion limit.

According to an embodiment, step 812 includes applying the digital signal and the sensor signal as arguments for a function. Receiving the sensor signal in step 810 may include performing an analog-to-digital (A/D) conversion on the sensor signal to form a digital sensor signal. Applying the digital signal and the sensor signal as arguments for a function may include using the digital signal and digital sensor signal to address a look-up table (LUT) or as parameters in a database query.

According to an embodiment, the digital sensor signal may be used to determine a page or region of a table (LUT or database) and the digital signal may select an address in the page or region.

In an alternative embodiment, applying the digital signal and the sensor signal as arguments for a function may include applying one or both of the digital signal and digital sensor signal as a parameter in an equation. According to an embodiment, the value of the function may be the fuel-air equivalence ratio.

According to an embodiment, the burner may be an industrial burner.

According to an embodiment, the fuel-oxidant equivalence ratio may be a fuel-air equivalence ratio.

Figure 9:
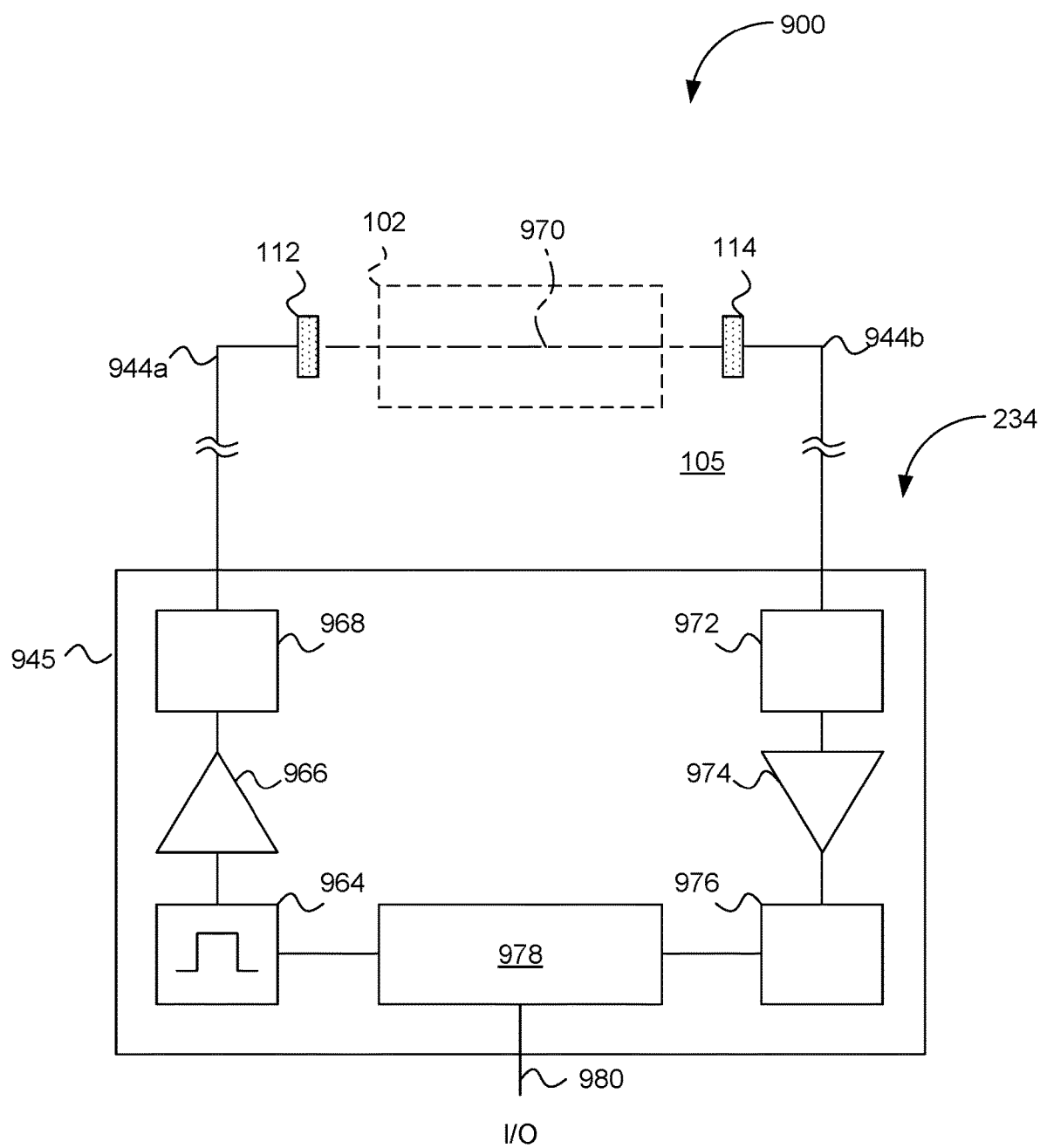
FIG. 9 is a diagram of a combustion system and sensor, according to an embodiment

FIG. 9 is a diagram of a combustion system 900 including a combustion sensor 234, according to an embodiment. The combustion sensor 234 may include, in a sensor controller 945, a waveform generator 964 that may be configured to output a time-varying voltage. An amplifier 966 (that can be inverting or non-inverting) may be operably coupled to the waveform generator 964, and may be configured to amplify a logic-level voltage from the waveform generator 964 to a broadcast voltage. An electrical filter 968 may be operably coupled to the amplifier 966, and may be configured to protect circuitry 966, 964, 978, 976, 974 in a signal controller from electrostatic discharge. The electrical filter 968 may be operably coupled to a first electrode 112 via a first electrical lead 944a. The first electrode 112 may be configured to broadcast the amplified waveform to a second electrode 114 through a gap spanning the perforated flame holder 102 as a broadcast signal, according to an embodiment.

A second electrical filter 972 (which may optionally be identical to the electrical filter 968) may be operably coupled to the second electrode 114 via a second electrical lead 944b, and may be configured to protect the circuitry 974, 976, 978, 964, 966 from electrostatic discharge, according to an embodiment.

A second amplifier 974 may be configured to raise a received voltage to a logic level voltage, according to an embodiment.

A receiver circuit 976 may be operatively coupled to the second amplifier 974, and may be configured to receive and digitize an amplified signal received by the second electrode 114. A signal analyzer 978 may be operatively coupled to the receiver circuit 976, according to an embodiment. The signal analyzer 978 may be configured to analyze digital data produced by the receiver circuit 976 and determine a fuel-oxidant equivalence ratio. The signal analyzer 978 can report the fuel-oxidant equivalence ratio, or a change in the fuel-oxidant equivalence ratio via a digital interface 980, according to an embodiment.

The sensor controller 945 can determine the fuel-oxidant equivalence ratio based on a signal received from the second electrode 114. The sensor controller 945 can determine the fuel-oxidant equivalence ratio based on a digital signal generated by performing an analog to digital conversion on the signal passed from the second electrode 114.

According to an embodiment, the sensor controller can apply the digital signal and a sensor signal as arguments for a function. The sensor signal can be a temperature signal. The sensor signal may also be converted to a digitized sensor signal before applying the sensor signal as arguments for the function. Applying the digital signal and the sensor signal as arguments for a function may include using the digital signal and digital sensor signal to address a look-up table (LUT) or as parameters in a database query. The look-up table or database may be included in a memory of the sensor controller 945, or may be external to the sensor controller 945.

The signal analyzer 978 may correspond to the controller 118 or may be separate from the controller 118.

In one embodiment, the electrical filters 968, 972 each include a vacuum bipolar electrode emitter operatively coupled to ground.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A system for measuring a fuel-oxidant equivalence ratio, comprising:
    at least one wall defining a gas volume, the gas including fuel and air;
    a gas ionization source configured to cause a formation of ions in the gas;
    a power supply configured to output a time-varying voltage;
    a first electrode disposed in the gas volume, operatively coupled to the power supply, and configured to carry the time-varying voltage;
    a second electrode, arranged to operatively couple to a signal from the first electrode through at least a portion of the gas volume;
    a receiver circuit operatively coupled to the second electrode and configured to receive the signal, the signal having a characteristic corresponding to the fuel-oxidant equivalence ratio within the gas volume; and
    a control circuit operatively coupled to the receiver circuit, configured to determine a value corresponding to the fuel-oxidant equivalence ratio.

2. The system for measuring a fuel-oxidant equivalence ratio of claim 1, wherein the gas ionization source occupies a physical volume within the gas volume; and wherein the first and the second electrodes are aligned such that the received signal has a characteristic corresponding to the fuel-oxidant equivalence ratio within the gas volume.

3. The system for measuring a fuel-oxidant equivalence ratio of claim 1, wherein the gas ionization source comprises at least one ionization electrode configured to ionize the gas in the gas volume, and wherein the at least one ionization electrode comprises a corona electrode.

4. The system for measuring a fuel-oxidant equivalence ratio of claim 1, wherein the gas ionization source comprises at least one ionization electrode configured to ionize the gas in the gas volume, and wherein the at least one ionization electrode comprises a dielectric barrier electrode.

5. The system for measuring a fuel-oxidant equivalence ratio of claim 1, wherein the gas volume comprises a tank headspace.

6. The system for measuring a fuel-oxidant equivalence ratio of claim 1, wherein the control circuit is further configured to automatically take corrective action when the fuel-oxidant equivalence ratio is determined to be within flammability limits.

7. A system for measuring a fuel-oxidant equivalence ratio, comprising:

at least one wall defining a gas volume, the gas including fuel and air;

a gas ionization source configured to cause a formation of ions in the gas;

a power supply configured to output a time-varying voltage;

a first electrode disposed in the gas volume, operatively coupled to the power supply, and configured to carry the time-varying voltage;

a second electrode, arranged to operatively couple to a signal from the first electrode through at least a portion of the gas volume;

a receiver circuit operatively coupled to the second electrode and configured to receive the signal, the signal having a characteristic corresponding to the fuel-oxidant equivalence ratio within the gas volume;

a control circuit operatively coupled to the receiver circuit, configured to determine a value corresponding to the fuel-oxidant equivalence ratio;

a purging system;

wherein the control circuit is configured to actuate the purging system to purge fuel vapor and/or oxidant from the gas volume when the fuel-oxidant equivalence ratio is determined to be within the flammability limits;

wherein the purging system comprises:
an inert gas source; and
a purge control valve;

wherein the control circuit is configured to actuate the purge control valve when the fuel-oxidant equivalence ratio is determined to be within the flammability limits.

8. The system for measuring a fuel-oxidant equivalence ratio of claim 1, wherein the wall comprises a flame arrestor.

9. The system for measuring a fuel-oxidant equivalence ratio of claim 1, wherein the gas ionization source comprises a burner, and wherein the burner comprises:
a flame holder aligned to receive a mixture of fuel from a fuel source and combustion air from a combustion air source.

10. The system for measuring a fuel-oxidant equivalence ratio of claim 9, wherein the burner further comprises a blower; and wherein the control circuit is configured to control the blower output responsive to detecting the fuel-oxidant equivalence ratio.

11. The system for measuring a fuel-oxidant equivalence ratio of claim 9, wherein the flame holder comprises a perforated flame holder.

12. The system for measuring a fuel-oxidant equivalence ratio of claim 11, wherein the perforated flame holder is a reticulated ceramic perforated flame holder.

13. The system for measuring a fuel-oxidant equivalence ratio of claim 12, wherein the perforated flame holder includes a plurality of reticulated fibers; wherein the perforations are formed as passages between the reticulated fibers; and wherein the perforated flame holder includes:
an input face;
an output face; and
a plurality of perforations extending between the input face and the output face.

14. The system for measuring a fuel-oxidant equivalence ratio of claim 13, wherein the perforations are branching perforations.

15. The system for measuring a fuel-oxidant equivalence ratio of claim 13, wherein the input face corresponds to an extent of the reticulated fibers proximal to the fuel nozzle, and wherein the output face corresponds to an extent of the reticulated fibers distal to the fuel nozzle.

16. The system for measuring a fuel-oxidant equivalence ratio of claim 12, wherein the perforated flame holder is configured to support at least a portion of the combustion reaction within the perforated flame holder between the input face and the output face.

17. The system for measuring a fuel-oxidant equivalence ratio of claim 1, further comprising a sensor operatively coupled to the control circuit, the sensor being configured to sense one or more of pressure and temperature, wherein the control circuit is configured to determine the fuel-oxidant equivalence ratio as a function of a value of the received signal in combination with a value of sensed temperature and/or pressure.

18. A method for measuring a fuel-oxidant equivalence ratio, comprising:

causing ion formation in a gas including fuel and oxidant;

applying a periodic voltage signal to a first electrode adjacent to the gas;

receiving a periodic response signal through the gas with a second electrode, the periodic response signal being produced according to a response of the ions to the periodic voltage signal;

converting the periodic response signal to a corresponding digital signal;

receiving a sensor signal corresponding to a parameter of the gas;

applying the digital signal and the sensor signal as arguments for a function; and determining a value of the function corresponding to the fuel-oxidant equivalence ratio.

19. The method for measuring a fuel-oxidant equivalence ratio of claim 18, further comprising:

holding a pressure of the gas constant;

wherein receiving the sensor signal comprises receiving a signal corresponding to a temperature of the gas.

20. The method for measuring a fuel-oxidant equivalence ratio of claim 18, further comprising:
holding a temperature of the gas constant;
wherein receiving the sensor signal comprises receiving a signal corresponding to a pressure of the gas.

21. The method for measuring a fuel-oxidant equivalence ratio of claim 18,
wherein the receiving the sensor signal comprises receiving a temperature signal corresponding to a temperature of the gas and receiving a pressure signal corresponding to a pressure of the gas.

22. The method for measuring a fuel-oxidant equivalence ratio of claim 18,
wherein the causing ion formation in the gas comprises operating an ionizer, and
wherein the operating the ionizer comprises applying a voltage to a corona electrode.

23. The method for measuring a fuel-oxidant equivalence ratio of claim 22,
wherein the corona electrode is disposed in a gas volume in which the first and the second electrodes are disposed.

24. The method for measuring a fuel-oxidant equivalence ratio of claim 18,
wherein the causing ion formation in the gas comprises operating an ionizer, and
wherein the operating the ionizer comprises applying a voltage to a dielectric barrier layer electrode.

25. The method for measuring a fuel-oxidant equivalence ratio of claim 18,
wherein the causing ion formation in the gas comprises operating an ionizer, and
wherein the causing ion formation in the gas further comprises operating the ionizer in a removed gas volume and conveying at least a portion of the ions from the removed gas volume to a gas volume in which the first and the second electrodes are disposed.

26. A method for measuring a fuel-oxidant equivalence ratio, comprising:
causing ion formation in a gas including fuel and oxidant;
applying a periodic voltage signal to a first electrode adjacent to the gas;
receiving a periodic response signal through the gas with a second electrode, the periodic response signal being produced according to a response of the ions to the periodic voltage signal;
converting the periodic response signal to a corresponding digital signal,
receiving a sensor signal corresponding to a parameter of the gas;
applying the digital signal and the sensor signal as arguments for a function; and
determining a value of the function corresponding to the fuel-oxidant equivalence ratio, wherein the causing ion formation in the gas comprises operating an ionizer, and further comprising:
determining a fuel-oxidant equivalence ratio within a combustion limit of the fuel; and
actuating a valve to change the fuel-air equivalence ratio to a ratio outside the combustion limit of the fuel;
wherein the actuating the valve comprises purging the gas with an inert gas.

27. The method for measuring a fuel-oxidant equivalence ratio of claim 26, wherein the inert gas includes nitrogen or carbon dioxide.

28. The method for measuring a fuel-oxidant equivalence ratio of claim 26, wherein the fuel comprises kerosene.

29. The method for measuring a fuel-oxidant equivalence ratio of claim 18, wherein the causing ion formation in the gas comprises operating an ionizer, and further comprising:
isolating the ions inside a grounded screen forming a flame arrestor.

30. The method for measuring a fuel-oxidant equivalence ratio of claim 18,
wherein the causing ion formation in the gas comprises supporting a combustion reaction in the gas.

31. The method for measuring a fuel-oxidant equivalence ratio of claim 30, further comprising:
outputting the fuel and the air toward a perforated flame holder;
wherein the causing ion formation in the gas comprises supporting the combustion reaction at least partially within the perforated flame holder.

32. The method for measuring a fuel-oxidant equivalence ratio of claim 31,
wherein the first electrode is disposed to output the periodic voltage signal toward the perforated flame holder; and
wherein the second electrode is disposed to receive the periodic response signal at least partially through the perforated flame holder.

33. The method for measuring a fuel-oxidant equivalence ratio of claim 30, further comprising:
determining a fuel-oxidant equivalence ratio to be at or near a combustion limit of the fuel; and
actuating a valve to change the fuel-air equivalence ratio to a valve nearer the center of the combustion limit;
wherein the determining the fuel-oxidant equivalence ratio near the combustion limit comprises determining the equivalence ratio to be outside the combustion limit.

34. The method for measuring a fuel-oxidant equivalence ratio of claim 18,
wherein the applying the digital signal and the sensor signal as arguments for a function comprises:
performing an analog-to-digital conversion on the sensor signal to form a digital sensor signal.

35. The method for measuring a fuel-oxidant equivalence ratio of claim 34,
wherein the applying the digital signal and the sensor signal as arguments for a function comprises:
using the digital signal and digital sensor signal to address a look-up table or as parameters in a database query.

36. The method for measuring a fuel-oxidant equivalence ratio of claim 35,
wherein the digital sensor signal is used to determine a page or region of a table and the digital signal selects an address in the page or region.

37. The method for measuring a fuel-oxidant equivalence ratio of claim 34,
wherein the applying the digital signal and the sensor signal as arguments for a function comprises applying at least one of the digital signal and the digital sensor signal as a parameter in an equation.

38. The method for measuring a fuel-oxidant equivalence ratio of claim 18,
wherein the value of the function is the fuel-oxidant equivalence ratio.

39. The method for measuring a fuel-oxidant equivalence ratio of claim 18, wherein the fuel-oxidant equivalence ratio is a fuel-air equivalence ratio.

40. The method for measuring a fuel-oxidant equivalence ratio of claim 18, wherein causing ion formation in a gas includes generating free electrons.

\* \* \* \* \*